(12) United States Patent
Okada et al.

(10) Patent No.: US 11,638,570 B2
(45) Date of Patent: May 2, 2023

(54) ULTRASONIC DIAGNOSTIC APPARATUS, PROBE SENSITIVITY MANAGEMENT SYSTEM, AND NON-TRANSITORY STORAGE MEDIUM

(71) Applicant: Canon Medical Systems Corporation, Otawara (JP)

(72) Inventors: Kengo Okada, Nasushiobara (JP); Fuminori Fujita, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 166 days.

(21) Appl. No.: 16/270,110

(22) Filed: Feb. 7, 2019

(65) Prior Publication Data
US 2019/0239854 A1   Aug. 8, 2019

(30) Foreign Application Priority Data

Feb. 7, 2018   (JP) .............................. JP2018-020229
Feb. 6, 2019   (JP) .............................. JP2019-019415

(51) Int. Cl.
*A61B 8/00*   (2006.01)
*A61B 8/08*   (2006.01)
*A61B 8/12*   (2006.01)

(52) U.S. Cl.
CPC .......... *A61B 8/4444* (2013.01); *A61B 8/4488* (2013.01); *A61B 8/12* (2013.01); *A61B 8/463* (2013.01); *A61B 8/5207* (2013.01)

(58) Field of Classification Search
CPC ..... A61B 8/4444; A61B 8/4488; A61B 8/463; A61B 8/5207; A61B 8/12; A61B 8/5269;
(Continued)

(56) References Cited

U.S. PATENT DOCUMENTS 5,517,994 A     5/1996   Burke et al.
6,370,480 B1 *  4/2002   Gupta ..................... A61B 8/00
                                                           702/39
(Continued)

FOREIGN PATENT DOCUMENTS

JP   H05-48906 U    6/1993
JP   8-238243       9/1996
(Continued)

OTHER PUBLICATIONS

Japanese Office Action dated Nov. 22, 2022, issued In Japanese Patent Application No. 2019-019415.

*Primary Examiner* — Joseph M Santos Rodriguez
*Assistant Examiner* — Kaitlyn E Sebastian
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe, a memory, and processing circuitry. The ultrasonic probe includes ultrasonic transducers. The processing circuitry measures first reflected wave signals generated by the ultrasonic probe at a first time point. The processing circuitry stores information concerning the first reflected wave signals in the memory. The processing circuitry measures second reflected wave signals generated by the ultrasonic probe at a second time point. The processing circuitry performs correction to suppress variations between the second reflected wave signals respectively generated by the ultrasonic transducers based on the information concerning the first and second reflected wave signals.

16 Claims, 19 Drawing Sheets

(58) Field of Classification Search
CPC ....... A61B 8/54; A61B 8/4483; G01S 7/5205; G01S 7/52077
See application file for complete search history.

(56) References Cited

U.S. PATENT DOCUMENTS

| | | | | |
|---|---|---|---|---|
| 2003/0199794 | A1* | 10/2003 | Sakurai | A61B 17/320092 601/2 |
| 2006/0241456 | A1 | 10/2006 | Karasawa | |
| 2014/0126791 | A1* | 5/2014 | Iimura | G01S 7/5205 382/128 |
| 2015/0087985 | A1* | 3/2015 | Yoshiara | A61B 8/481 600/443 |
| 2016/0331348 | A1* | 11/2016 | Nakatsuji | G06T 7/00 |
| 2017/0090024 | A1* | 3/2017 | Kitchens, II | A61B 8/0858 |
| 2017/0290567 | A1* | 10/2017 | Fujita | A61B 8/14 |

FOREIGN PATENT DOCUMENTS

| | | |
|---|---|---|
| JP | 2000-139905 | 5/2000 |
| JP | 2004-248860 | 9/2004 |
| JP | 2006-217934 | 8/2006 |
| JP | 2008-212235 | 9/2008 |
| JP | 2009-153675 | 7/2009 |
| JP | 2009-178262 | 8/2009 |
| JP | 2010-213983 | 9/2010 |
| JP | 2014-046062 A | 3/2014 |
| JP | 2017-185129 A | 10/2017 |

* cited by examiner

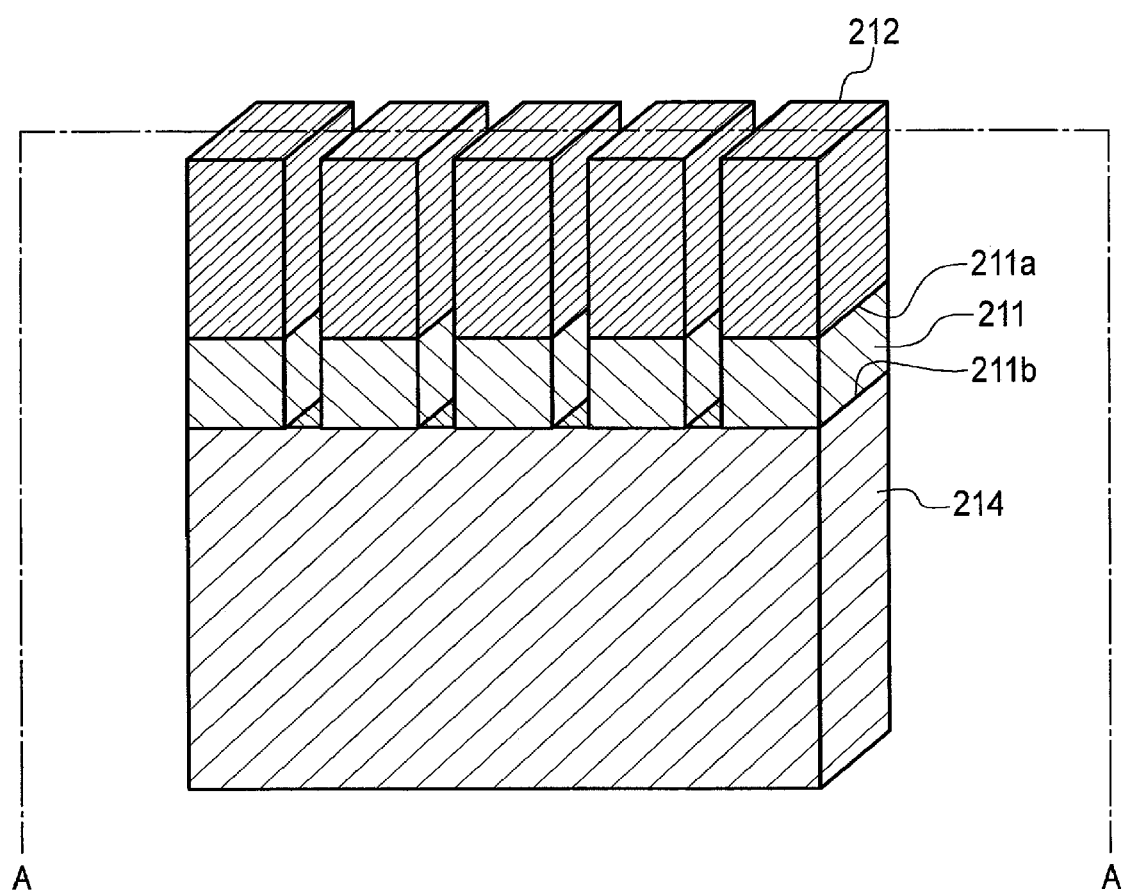
F I G. 2

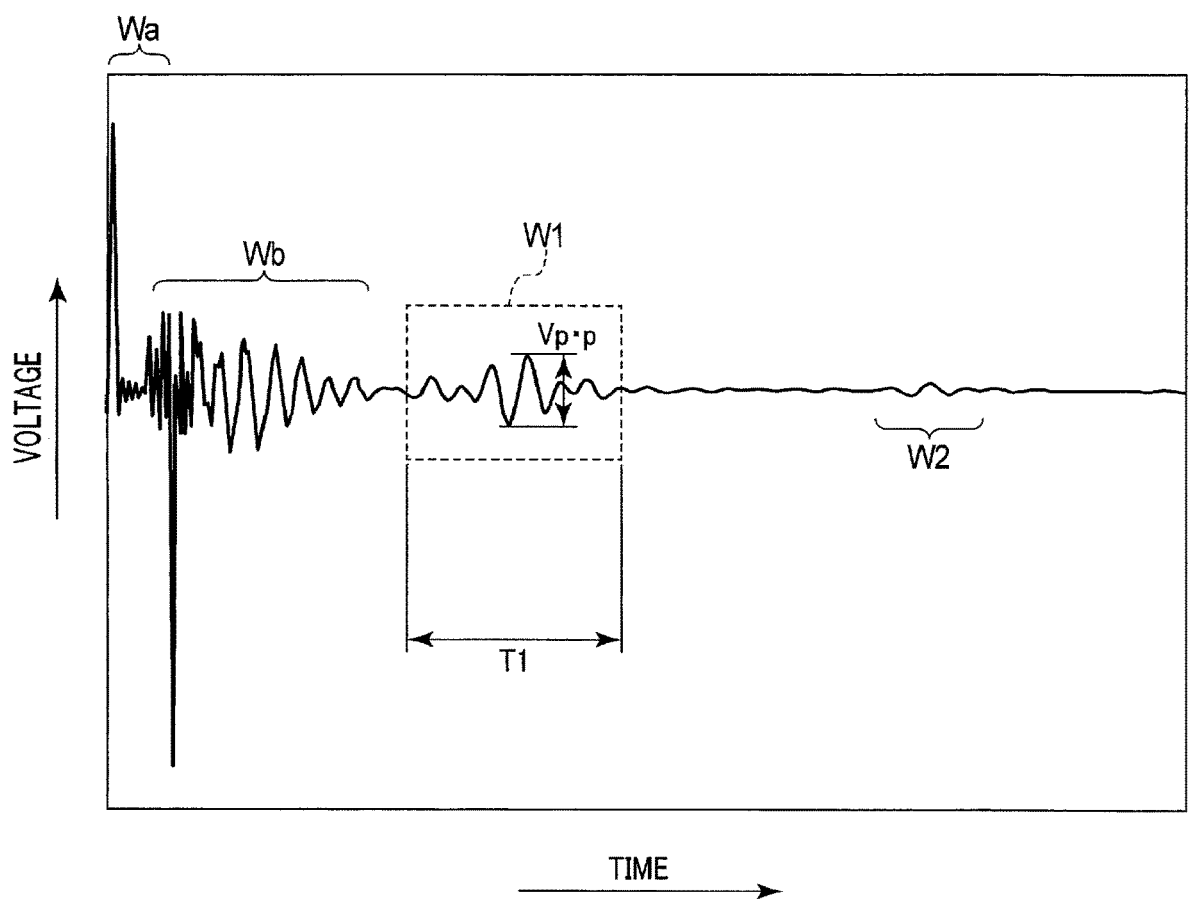
F I G. 5

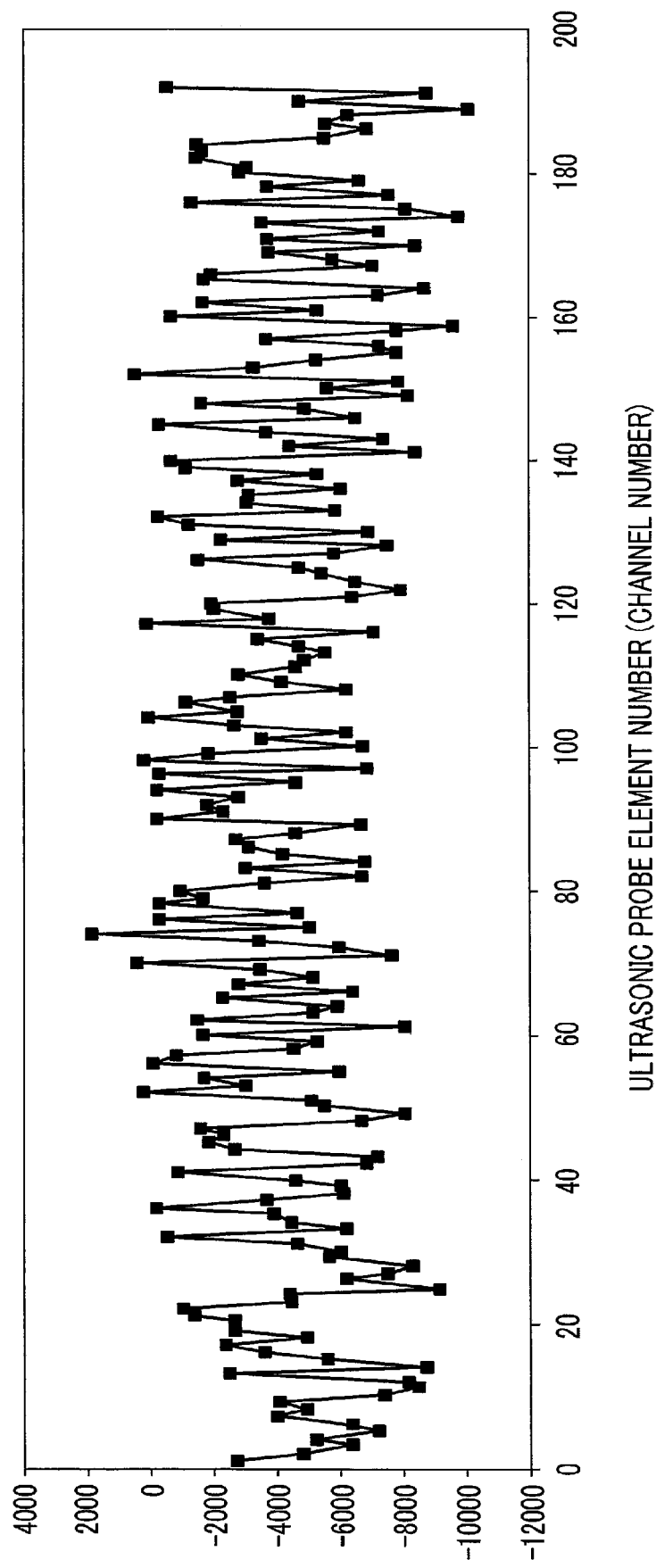
F I G. 9

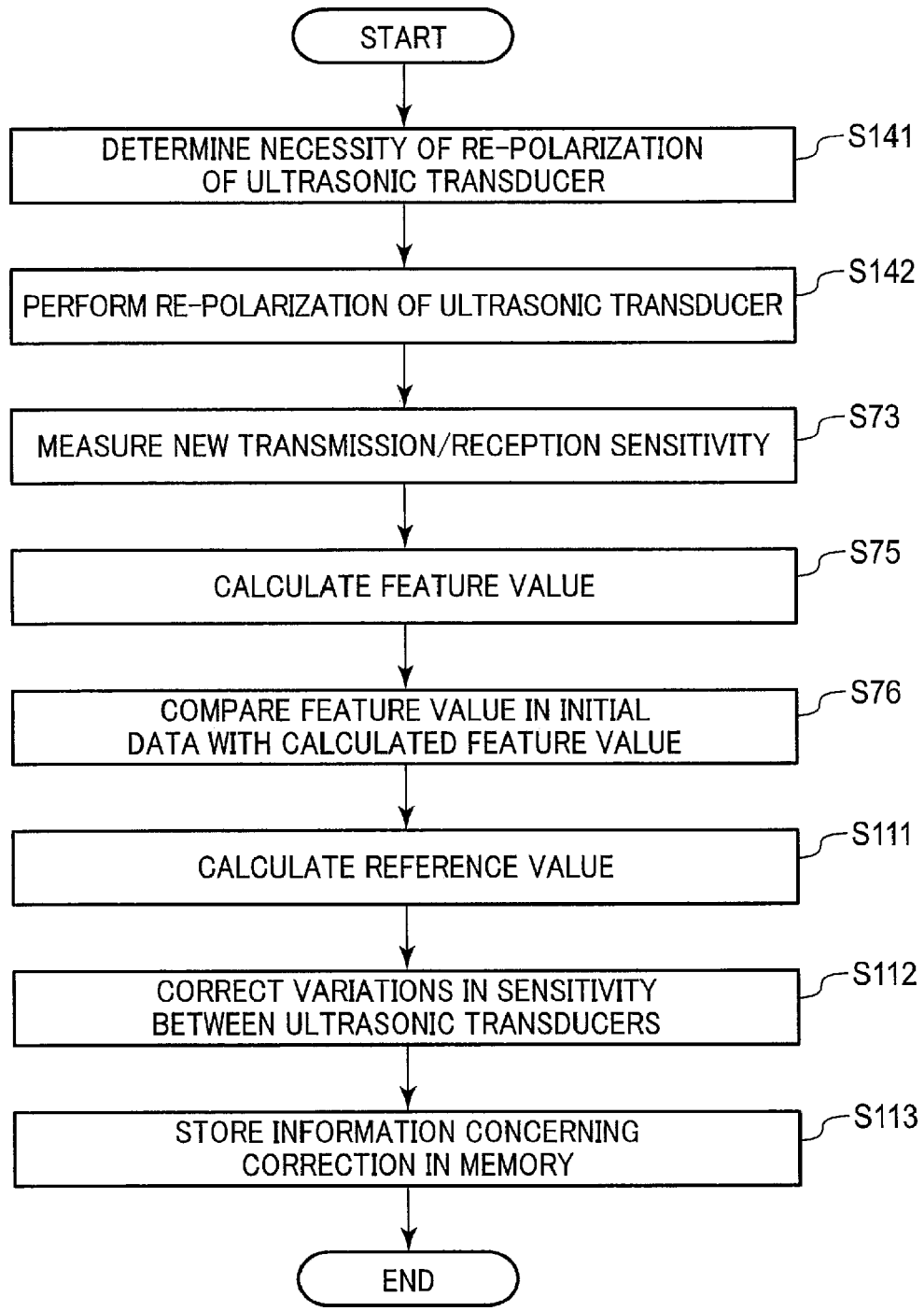
F I G. 14

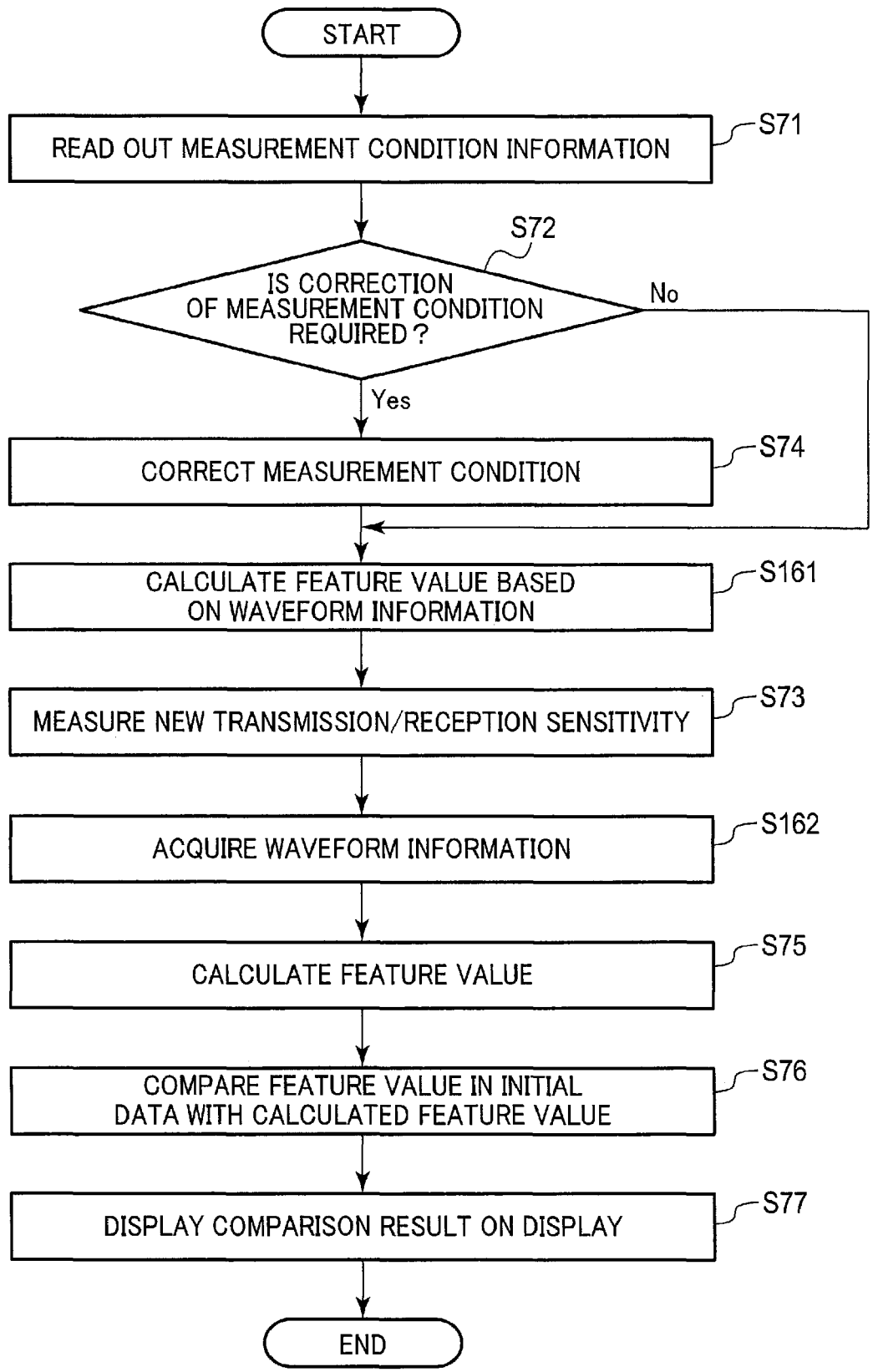
F I G. 16

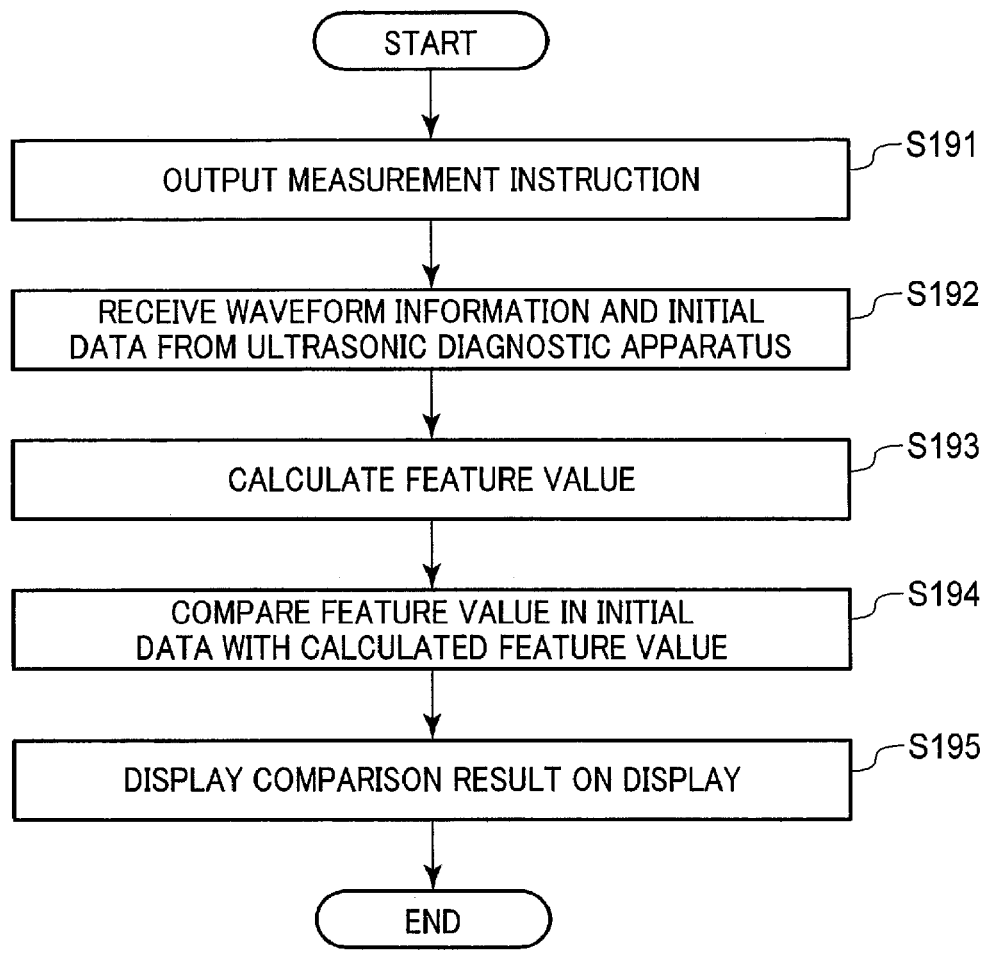
F I G. 19
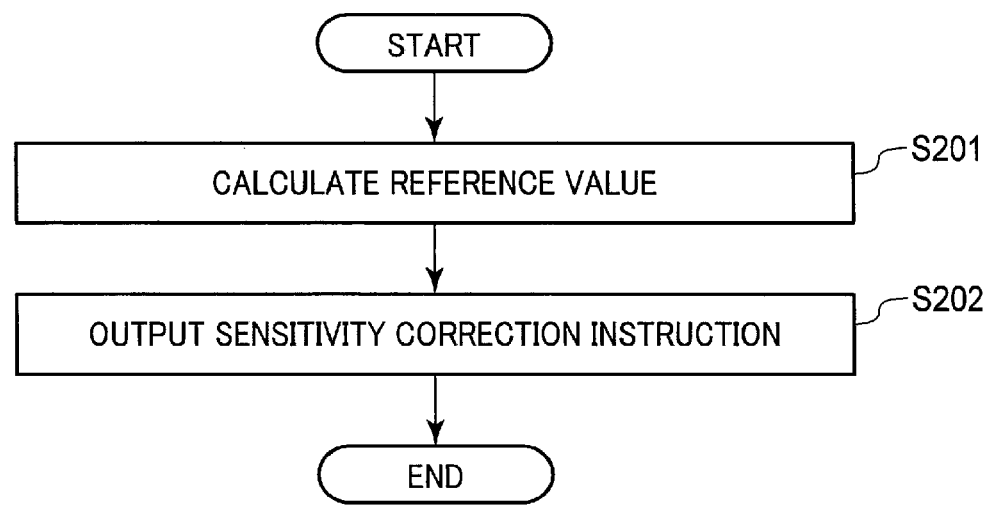
F I G. 20

ULTRASONIC DIAGNOSTIC APPARATUS, PROBE SENSITIVITY MANAGEMENT SYSTEM, AND NON-TRANSITORY STORAGE MEDIUM

CROSS-REFERENCE TO RELATED APPLICATIONS

This application is based upon and claims the benefit of priority from the prior Japanese Patent Application No. 2018-020229, filed Feb. 7, 2018 and No. 2019-19415, filed Feb. 6, 2019, the entire contents of both which are incorporated herein by reference.

FIELD

Embodiments described herein relate generally to an ultrasonic diagnostic apparatus, a probe sensitivity management system, and a non-transitory storage medium.

BACKGROUND

An ultrasonic diagnostic apparatus causes an ultrasonic probe having an array of a plurality of ultrasonic transducers to emit ultrasonic waves to an object and receive the reflected waves of the transmitted ultrasonic waves.

A polarization treatment for causing polarization is applied to each ultrasonic transducer to provide piezoelectricity. However, the polarization characteristics of ultrasonic transducers provided for an ultrasonic probe deteriorate due to aging and the like. In this manner, the sensitivity of the ultrasonic probe may deteriorate as ultrasonic transducers deteriorate due to aging. This may affect the quality of ultrasonic images generated by the ultrasonic diagnostic apparatus.

BRIEF DESCRIPTION OF THE DRAWING

FIG. 2 is a perspective view of the ultrasonic transducer unit of the probe head of an ultrasonic probe shown in FIG. 1;

FIG. 5 is a graph representing a reflected wave signal received by the apparatus main body shown in FIG. 1;

FIG. 9 is a graph representing the differences between sensitivity peak values as initial data and feature values acquired at a predetermined timing;

FIG. 14 is a flowchart when the control circuitry shown in FIG. 1 corrects the sensitivity of the ultrasonic probe through the re-polarization of the ultrasonic transducers;

FIG. 16 is a flowchart when the control circuitry shown in FIG. 1 causes the display to display information concerning the sensitivity of the ultrasonic probe;

FIG. 19 is a flowchart when the control circuitry shown in FIG. 18 causes a display to display information concerning the sensitivity of the ultrasonic probe; and FIG. 20 is a flowchart when the control circuitry shown in FIG. 18 instructs the ultrasonic diagnostic apparatus to perform sensitivity correction of the ultrasonic probe.

DETAILED DESCRIPTION

In general, according to one embodiment, an ultrasonic diagnostic apparatus includes an ultrasonic probe, a memory, and processing circuitry. The ultrasonic probe includes a plurality of ultrasonic transducers. The processing circuitry measures first reflected wave signals generated by the ultrasonic probe at a first time point. The processing circuitry stores information concerning the first reflected wave signals in the memory. The processing circuitry measures second reflected wave signals generated by the ultrasonic probe at a second time point after the first time point. The processing circuitry performs correction to suppress variations between the second reflected wave signals respectively generated by the plurality of ultrasonic transducers based on the information concerning the first reflected wave signals stored in the memory and information concerning the second reflected wave signals acquired based on the measurement of the second reflected wave signals.

Embodiments will be described below with reference to the accompanying drawings.

First Embodiment

Figure 1:
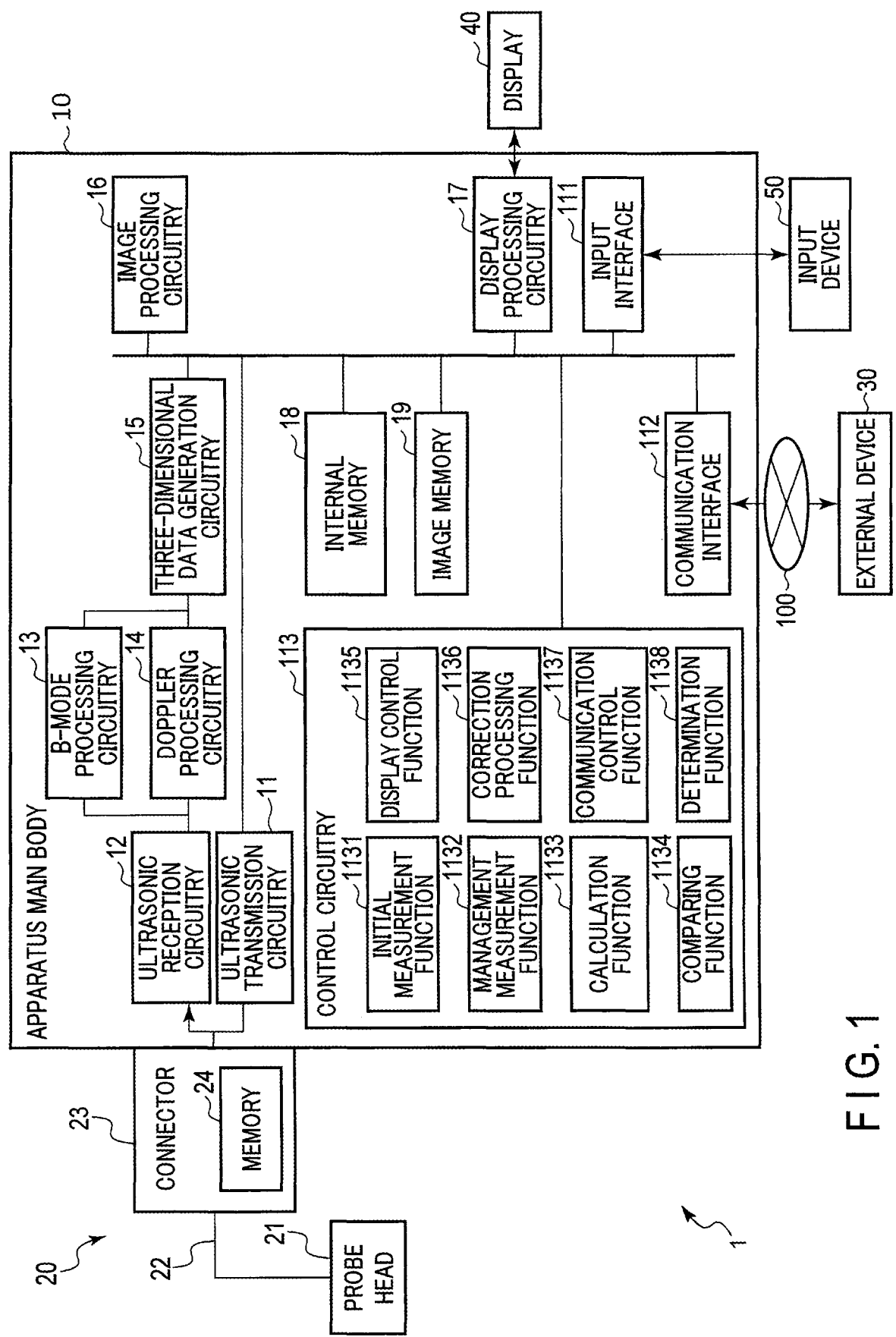
FIG. 1 is a block diagram showing the arrangement of an ultrasonic diagnostic apparatus according to the first embodiment.

FIG. 1 is a block diagram showing an example of the arrangement of an ultrasonic diagnostic apparatus 1 according to the first embodiment. The ultrasonic diagnostic apparatus 1 shown in FIG. 1 includes an apparatus main body 10 and an ultrasonic probe 20. The apparatus main body 10 is connected to an external device 30 via a network 100. The apparatus main body 10 is connected to a display 40 and an input device 50.

The ultrasonic probe 20 includes a probe head 21, a cable 22, and a connector 23. The probe head 21 is electrically connected to the apparatus main body 10 via the cable 22 and the connector 23. The connector 23 is formed so as to be detachable from the apparatus main body 10.

The probe head 21 includes a plurality of ultrasonic transducers (piezoelectric transducers) made of a single crystal or polycrystalline piezoelectric material. The ultrasonic transducers generate ultrasonic waves based on driving signals supplied from ultrasonic transmission circuitry 11 of the apparatus main body 10. When the ultrasonic transducers generate ultrasonic waves, the probe head 21 transmits ultrasonic waves to a living body.

When the probe head 21 transmits ultrasonic waves to the living body, the transmitted ultrasonic waves are sequentially reflected by a discontinuity surface of acoustic impedance of tissue in the living body, and are received as reflected wave signals by the plurality of ultrasonic transducers of the probe head 21. The amplitude of each received reflected wave signal depends on an acoustic impedance difference on the discontinuity surface by which the ultrasonic wave is reflected. The reflected wave signal produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect. Each ultrasonic transducer converts a reflected wave signal into an electrical signal and transmits it to the apparatus main body 10.

The ultrasonic probe 20 also includes memory 24. The memory 24 includes, for example, a storage medium in which written data can be written and from which data can be read out, such as a semiconductor memory. The memory 24 is provided, for example, in the probe head 21 or the connector 23. For example, measurement condition information concerning measurement conditions is written in the memory 24 in advance. The measurement conditions include, for example, conditions for the measurement of the sensitivity of the ultrasonic probe 20 for each channel. Measurement condition information is read out from the memory 24 in response to a request, and is output to the request source. Measurement condition information is updated as needed.

Note that the ultrasonic probe 20 according to this embodiment is, for example, a one-dimensional array probe having a plurality of ultrasonic transducers arrayed along a predetermined direction. However, the ultrasonic probe used is not limited to this, and the ultrasonic probe 20 may be a two-dimensional array probe (a probe having a plurality of ultrasonic transducers arrayed in the form of a two-dimensional matrix) or a mechanical 4D probe (a probe which can execute ultrasonic scanning while mechanically swinging an ultrasonic transducer array in a direction perpendicular to the array direction) as a probe which can acquire volume data.

FIG. 1 exemplarily shows only the connection relationship between the ultrasonic probe 20 and the apparatus main body 10 which are used for imaging. However, a plurality of ultrasonic probes can be connected to the apparatus main body 10. A user can arbitrarily select, for imaging, any one of the plurality of ultrasonic probes connected to the apparatus main body 10 by a switching operation.

The apparatus main body 10 shown in FIG. 1 is an apparatus that generates an ultrasonic image based on reflected wave signals received by the ultrasonic probe 20. As shown in FIG. 1, the apparatus main body 10 includes the ultrasonic transmission circuitry 11, ultrasonic reception circuitry 12, B-mode processing circuitry 13, Doppler processing circuitry 14, three-dimensional data generation circuitry 15, image processing circuitry 16, display processing circuitry 17, internal memory 18, an image memory 19 (cine memory), an input interface 111, a communication interface 112, and control circuitry 113.

The ultrasonic transmission circuitry 11 is a processor that supplies a driving signal to the ultrasonic probe 20. The ultrasonic transmission circuitry 11 is implemented by, for example, trigger generation circuitry, delay circuitry, and pulser circuitry. The trigger generation circuitry repetitively generates rate pulses for the formation of transmission ultrasonic waves at a predetermined rate frequency. The delay circuitry gives each rate pulse generated by the trigger generation circuitry the delay time for each piezoelectric transducer necessary to focus ultrasonic waves from the ultrasonic probe 20 into a beam and determine a transmission directivity. The pulser circuitry applies driving signals (driving voltages) to the plurality of ultrasonic transducers provided for the ultrasonic probe 20 at the timing based on rate pulses. When, for example, each of a plurality of ultrasonic transducers is set to function as a transmission/reception channel, the pulser circuitry respectively applies driving signals to the plurality of ultrasonic transducers. In addition, when a preset number of ultrasonic transducers function as transmission/reception channels, the pulser circuitry applies driving signals to the ultrasonic transducers. The delay circuitry can arbitrarily adjust a transmission direction from a piezoelectric transducer surface by changing the delay time given to each rate pulse.

The ultrasonic reception circuitry 12 is a processor that generates reception signals by applying various types of processing to the reflected wave signals received by the ultrasonic probe 20. The ultrasonic reception circuitry 12 is implemented by, for example, amplification circuitry, an A/D converter, reception delay circuitry, and an adder. The amplification circuitry performs gain correction processing by amplifying reflected wave signals received by the ultrasonic probe 20 for each channel. The A/D converter converts gain-corrected reflected wave signals into digital signals. The reception delay circuitry gives digital signals delay times necessary to determine reception directivity. The adder performs adds a plurality of digital signals to which the delay times are given. The addition processing by the adder generates a reception signal whose reflection component from a direction corresponding to the reception directivity is enhanced.

The B-mode processing circuitry 13 is a processor that generates B-mode data based on the reception signal received by the ultrasonic reception circuitry 12. The B-mode processing circuitry 13 performs envelope detection processing, logarithmic amplification processing, and the like for the reception signal received from the ultrasonic reception circuitry 12 to generate data (B-mode data) whose signal intensity is expressed by a luminance level. The generated B-mode data is stored in a RAW data memory (not shown) as B-mode RAW data on two-dimensional ultrasonic scanning lines.

The Doppler processing circuitry 14 is a processor that generates a Doppler waveform and Doppler data based on the reception signals received from the ultrasonic reception circuitry 12. The Doppler processing circuitry 14 extracts a blood flow signal from a reception signal, generates a Doppler waveform from the extracted blood flow signal, and generates data (Doppler data) by extracting information such as an average velocity, variance, and power at multiple points from the blood flow signal. The generated Doppler data is stored in the RAW data memory (not shown) as Doppler RAW data on two-dimensional ultrasonic scanning lines.

The three-dimensional data generation circuitry 15 is a processor that generates three-dimensional image data based on the data generated by the B-mode processing circuitry 13 and the Doppler processing circuitry 14. The three-dimensional data generation circuitry 15 generates, for example, two-dimensional image data constituted by pixels or three-dimensional image data (to be referred to as volume data hereinafter) constituted by voxels based on B-mode RAW data stored in the RAW data memory.

The image processing circuitry 16 is a processor that applies predetermined image processing to two-dimensional image data or volume data. The predetermined image processing includes, for example, volume rendering, MPR (Multi Planar Reconstruction), and MIP (Maximum Intensity Projection). In addition, for the purpose of reducing noise or smooth concatenation of images, the image processing circuitry 16 performs spatial smoothing upon inserting a two-dimensional filter after the image processing.

The display processing circuitry 17 is a processor that converts various types of image data generated and processed by the image processing circuitry 16 into video signals. More specifically, the display processing circuitry 17 executes various types of processing associated with a dynamic range, luminance (brightness), contrast, y curve correction, RGB conversion, and the like for various types of image data generated and processed by the image processing circuitry 16, thereby converting image data into video signals. The display processing circuitry 17 causes the display 40 to display video signals. Note that the display processing circuitry 17 may generate a user interface (GUI: Graphical User Interface) for allowing the operator to input various types of instructions with the input interface 111 and cause the display 40 to display the GUI. It is possible to use as appropriate, as the display 40, for example, a CRT display, liquid crystal display, organic EL display, LED display, plasma display, or another arbitrary display known in this technical field.

The internal memory 18 includes, for example, a storage medium or the like that is readable by a processor, such as a magnetic or optical storage medium or semiconductor memory. The internal memory 18 stores a program for implementing ultrasonic transmission/reception, a program for performing image processing, a program for performing display processing, a program for managing the sensitivity of the ultrasonic probe 20, and the like. The internal memory 18 stores data such as diagnosis information (e.g., patient ID, findings by doctors, and the like), a diagnostic protocol, transmission conditions, reception conditions, signal processing conditions, image generation conditions, image processing conditions, a body mark generation program, display conditions, and a conversion table for setting, in advance, the range of color data used for visualization for each diagnosis region. Note that the above programs and data may be stored in the internal memory 18 in advance. In addition, the programs and data may be stored in, for example, a non-transitory storage medium and distributed, and may be read out from the non-transitory storage medium and installed in the internal memory 18. The internal memory 18 also stores measurement apparatus information such as an identification ID that can specify the apparatus main body 10.

The internal memory 18 also stores the two-dimensional image data and volume data generated by the three-dimensional data generation circuitry 15, the image data generated and processed by the image processing circuitry 16, and the image data generated by the control circuitry 113 in accordance with storage operations input via the input interface 111. The internal memory 18 can also transfer stored data to the external device 30 via the communication interface 112.

The internal memory 18 may be a driving device or the like that reads/writes various types of information from/to a portable storage medium such as a CD-ROM drive, a DVD drive, or a flash memory. The internal memory 18 can write stored data in a portable storage medium and cause the external device 30 to store data via the portable storage medium.

The image memory 19 includes a storage medium or the like that is readable by a processor, such as a magnetic or optical storage medium or semiconductor memory. The image memory 19 saves image data corresponding to a plurality of frames immediately before a freeze operation input via the input interface 111. Image data stored in the image memory 19 is, for example, continuously displayed (cine-displayed).

The internal memory 18 and the image memory 19 each are not always implemented by an independent memory. The internal memory 18 and the image memory 19 may be implemented by a single memory. Alternatively, the internal memory 18 and the image memory 19 each may be implemented by a plurality of memories.

The input interface 111 receives various types of instructions from the user via the input device 50. The input device 50 is, for example, a mouse, keyboard, panel switch, slider switch, trackball, rotary encoder, operation panel, or touch command screen (TCS). The input interface 111 is connected to the control circuitry 113 via, for example, a bus. The input interface 111 converts an operation instruction input from the operator into an electrical signal and outputs the electrical signal to the control circuitry 113. Note that in this embodiment, the input interface 111 is not limited to one that is connected to a physical operation component such as a mouse or keyboard. Examples of the input interface 111 include processing circuitry that receives an electrical signal corresponding to an operation instruction input from an external input device provided independently of the ultrasonic diagnostic apparatus 1 and outputs the electrical signal to the control circuitry 113.

The communication interface 112 is connected to the external device 30 via the network 100 or the like to perform data communication with the external device 30. The external device 30 is, for example, a database such as a PACS (Picture Archiving and Communication System) as a system for managing various types of medical image data or an electronic health card system for managing electronic health cards attached to medical images. The external device 30 is, for example, an X-ray CT (Computed Tomography) apparatus, MRI (Magnetic Resonance Imaging) apparatus, nuclear medicine diagnostic apparatus, X-ray diagnostic apparatus, or one of various types of medical image diagnostic apparatuses other than the ultrasonic diagnostic apparatus 1 according to this embodiment. Although the communication standard used for the external device 30 can be any standard, for example, DICOM (digital imaging and communication in medicine) can be used.

The control circuitry 113 is, for example, a processor that functions as the central unit of the ultrasonic diagnostic apparatus 1. The control circuitry 113 executes programs stored in the internal memory 18 to implement functions corresponding to the programs. More specifically, the control circuitry 113 executes the program stored in the internal memory 18 and configured to manage the sensitivity of the ultrasonic probe 20 to implement a function corresponding to the program. The control circuitry 113 includes, for example, an initial measurement function 1131, a management measurement function 1132, a calculation function 1133, a comparing function 1134, a display control function 1135, and a correction processing function 1136.

The initial measurement function 1131 is a function of acquiring initial data about the ultrasonic probe 20. More specifically, for example, the control circuitry 113 executes the initial measurement function 1131 at a predetermined time point during a period from the manufacture of the ultrasonic diagnostic apparatus 1 to shipment or after the shipment. Upon executing the initial measurement function 1131, the control circuitry 113 reads out measurement condition information stored in the memory 24 at the time of the manufacture of the ultrasonic probe 20. The measurement condition information stored at the time of manufacture includes, for example, conditions for the measurement of the sensitivity of the ultrasonic probe 20 for each channel. More specifically, the measurement conditions in this case include, for example, the driving voltage of the pulser circuitry of the ultrasonic transmission circuitry 11. These conditions may also include a driving frequency. The conditions may also include an applied waveform. These conditions may also include the gain of the amplification circuitry of the ultrasonic reception circuitry 12. These conditions may also include a waveform acquisition interval (gate position). These conditions may also include a probe ID identifying the ultrasonic probe 20. These conditions may also include the number of channels in the ultrasonic probe 20. These conditions may also include probe noise data in the ultrasonic probe 20. The probe noise data is data unique to the ultrasonic probe, and data representing a waveform other than a surface reflection wave. Note that information included in the measurement conditions is not limited to these conditions.

The control circuitry 113 controls the ultrasonic transmission circuitry 11 based on readout measurement condition information. The control circuitry 113 acquires a reflected wave signal for each channel under the setting of acquired measurement conditions. The control circuitry 113 adds information representing an environment in which the reflected wave signals are measured to the measurement condition information stored in the memory 24. In this case, the information added to the measurement condition information includes, for example, measurement date and time. This information may also include measurement apparatus information that can specify the apparatus main body 10 that has executed measurement. The information may also include a temperature in the ultrasonic probe 20. The control circuitry 113 stores, in the memory 24, feature values calculated by the calculation function 1133 based on the acquired reflected wave signals as initial data.

The management measurement function 1132 is a function of measuring the sensitivity of the ultrasonic probe 20. More specifically, for example, the control circuitry 113 executes the management measurement function 1132 at an arbitrary timing after shipment. Upon executing the management measurement function 1132, the control circuitry 113 controls the ultrasonic transmission circuitry 11 based on measurement condition information stored in the memory 24 of the ultrasonic probe 20. The control circuitry 113 acquires a reflected wave signal for each channel under the setting of measurement conditions.

The calculation function 1133 is a function of calculating feature values based on acquired reflected wave signals. More specifically, for example, the control circuitry 113 executes the calculation function 1133 upon acquisition of a reflected wave signal for each channel. Upon executing the calculation function 1133, the control circuitry 113 calculates a feature value by analyzing the reflected wave system of the acquired reflected wave signal. Assumed feature values include the sensitivity peak value, center frequency, wave train length, and fractional bandwidth of each channel. Assumed feature values also include a representative value such as an average value or standard deviation of above values for each channel. The control circuitry 113 calculates at least one of these values as a feature value.

The comparing function 1134 is a function of comparing the feature values acquired at two different time points. More specifically, upon executing the comparing function 1134, the control circuitry 113 compares feature values included in the initial data stored in the memory 24 with feature values obtained by measurement. Note that time points for comparison targets are not limited to these time points. The control circuitry 113 may compare feature values at two time points corresponding to instructions input from the input interface 111. For example, the control circuitry 113 may compare feature values acquired at a given time point with feature values acquired thereafter.

The display control function 1135 is a function of displaying a comparison result on the display 40. More specifically, for example, upon executing the display control function 1135, the control circuitry 113 controls the display processing circuitry 17 so as to cause the display 40 to display a feature value comparison result.

The correction processing function 1136 is a function of performing correction to suppress variations in sensitivity between the ultrasonic transducers of the ultrasonic probe 20. More specifically, for example, upon executing the correction processing function 1136, the control circuitry 113 corrects variations in sensitivity between the ultrasonic transducers provided for the ultrasonic probe 20 based on a feature value comparison result. For example, the control circuitry 113 changes the driving voltage of the pulser circuitry of the ultrasonic transmission circuitry 11 so as to make the feature value to be obtained by measurement satisfy a requirement concerning a predetermined reference value. The control circuitry 113 stores the changed driving voltage of the pulser circuitry in addition to the measurement condition information stored in the memory 24.

Note that the processing for correcting variations in sensitivity between ultrasonic transducers is not limited to a change in the driving voltage of the pulser circuitry. The control circuitry 113 may change the gain of the amplification circuitry of the ultrasonic reception circuitry 12 based on the reference value.

The control circuitry 113 may correct variations in sensitivity between ultrasonic transducers by re-polarizing ultrasonic transducers. For example, the control circuitry 113 controls the pulser circuitry of the ultrasonic transmission circuitry 11 to load, for a preset period, a DC or AC voltage with a predetermined magnitude from the pulser circuitry to each ultrasonic transducer.

Figure 3:
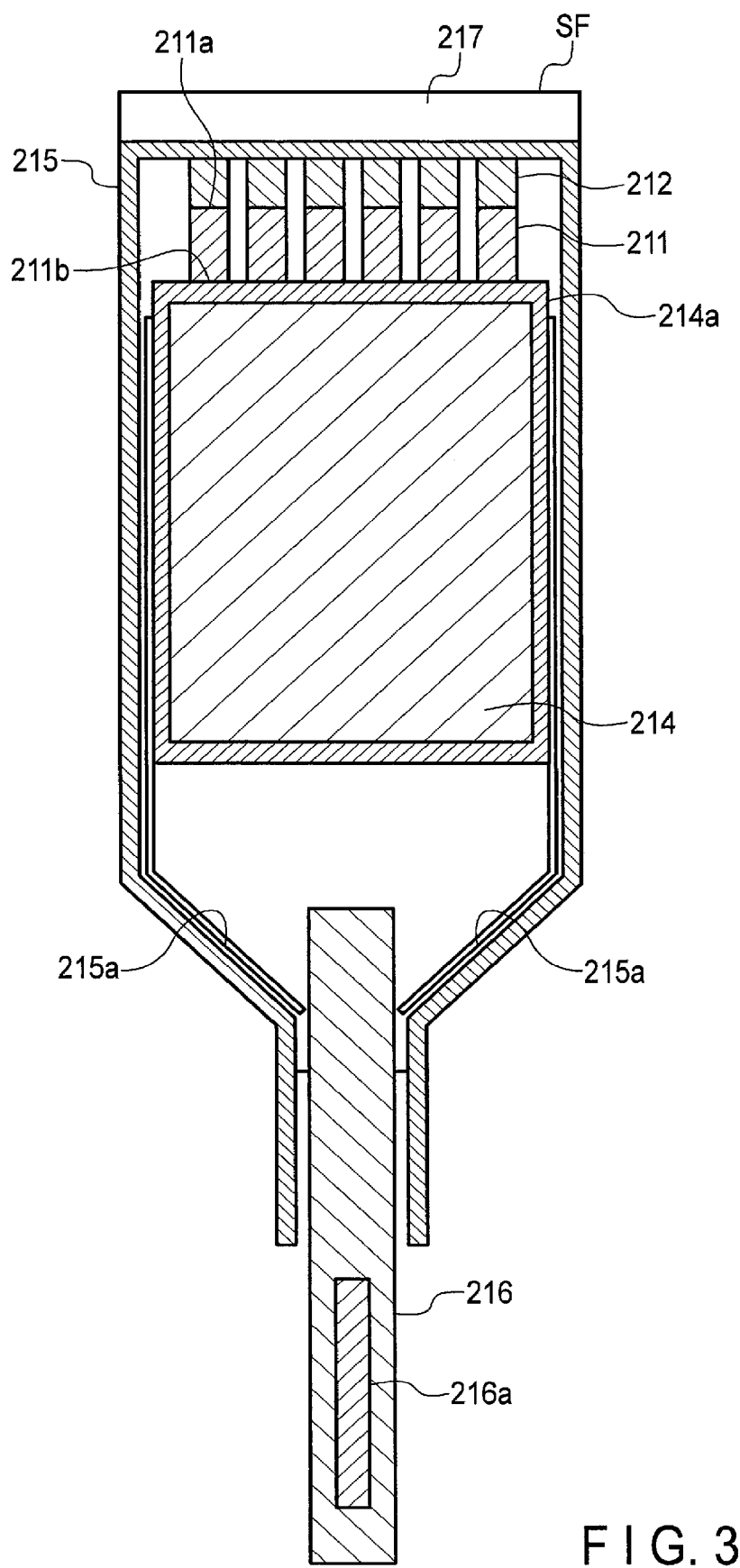
FIG. 3 is a sectional view of the ultrasonic transducer unit shown in FIG. 2.

FIGS. 2 and 3 are views showing an example of the arrangement of the ultrasonic transducer unit of the probe head 21 of the ultrasonic probe 20 shown in FIG. 1. FIG. 2 shows an example of a perspective view of the ultrasonic transducer unit. FIG. 3 is an example of a sectional view of the ultrasonic transducer unit taken along cut line A-A in FIG. 2. FIG. 2 schematically exemplifies the ultrasonic transducer unit while omitting the illustration of a flexible wiring board 215, a substrate 216, and an acoustic lens 217 shown in FIG. 3.

As exemplified by FIGS. 2 and 3, the ultrasonic transducer unit includes a plurality of ultrasonic transducers 211, an acoustic matching layer 212, a back surface load member (backing member) 214, the flexible wiring board 215, the substrate 216, and the acoustic lens 217.

In this embodiment, the ultrasonic transducers 211 are one-dimensionally arrayed on a predetermined surface of the back surface load member 214. A first electrode 211a is provided on a surface (ultrasonic radiation surface) of each ultrasonic transducer 211 from which ultrasonic waves are emitted. A second electrode 211b, which can have a potential independent of the potential of the first electrode 211a, is provided on a surface (back surface) of the ultrasonic transducer 211 which is located on the opposite side to the ultrasonic radiation surface. The ultrasonic transducer 211 is driven by a driving signal from transmission/reception circuitry 216a provided on the substrate 216 to emit ultrasonic waves from the surface located on the first electrode 211a side. In addition, upon receiving a reflected wave, the ultrasonic transducer 211 converts the received reflected wave into a reflected wave signal, and outputs the converted reflected wave signal from the first electrode 211a.

A surface of each second electrode 211b which is located on the opposite side to the ultrasonic transducer 211 is electrically connected to a conductive film 214a of the back surface load member 214.

The acoustic matching layer 212 is provided on a surface of each first electrode 211a which is located on the opposite side to the ultrasonic transducer 211. The acoustic matching layer 212 is an acoustic matching layer including at least one layer. The acoustic matching layer 212 reduces the acoustic impedance mismatching between the ultrasonic transducer 211 and an object so as to allow ultrasonic waves emitted from the ultrasonic transducer 211 to efficiently enter the living body.

The flexible wiring board 215 is electrically connected to a surface of the acoustic matching layer 212 which is located on the opposite side to the ultrasonic transducer 211. The flexible wiring board 215 is an example of a wiring board having flexibility. The flexible wiring board 215 is, for example, a double-sided FPC (Flexible printed circuits) or single-sided FPC. The flexible wiring board 215 is provided with wiring patterns respectively connected to the plurality of ultrasonic transducers 211. Each wiring pattern is connected to the acoustic matching layer 212 electrically connected to each target ultrasonic transducer 211 to which the wiring pattern is connected. With this arrangement, the first electrode 211a of each ultrasonic transducer 211 is electrically connected to the transmission/reception circuitry 216a via the acoustic matching layer 212 and the flexible wiring board 215.

With reference to FIGS. 2 and 3, the case where the wiring patterns provided on the flexible wiring board 215 are connected to the acoustic matching layer 212 have been described as an example. However, the ultrasound transducer may be designed to use 214a as a flexible printed board while omitting the flexible wiring board 215.

The back surface of the flexible wiring board 215 is provided with a wiring pattern 215a in an exposed state. The wiring pattern 215a is a ground pattern having a predetermined reference potential. The flexible wiring board 215 is bent to be almost parallel to a side surface of the back surface load member 214.

The wiring pattern 215a is electrically connected to the conductive film 214a of the back surface load member 214. Connecting the wiring pattern 215a to the conductive film 214a will electrically connect the second electrode 211b of each ultrasonic transducer 211 to the transmission/reception circuitry 216a via the wiring pattern 215a and the conductive film 214a.

The back surface load member 214 suppresses the propagation of ultrasonic waves from each ultrasonic transducer 211 to the back surface direction (backward). The back surface load member 214 is a non-conductor including a metal such as tungsten, a resin (e.g., epoxy resin) filled with a metal oxide such as alumina or zinc oxide, rubber, or the like. The conductive film 214a having conductivity is formed on the surface of the back surface load member 214 by means such as plating.

The substrate 216 has the transmission/reception circuitry 216a. The transmission/reception circuitry 216a is connected to a wiring pattern (not shown) provided on the substrate 216. The wiring pattern connected to the transmission/reception circuitry 216a is electrically connected to the wiring pattern provided on the flexible wiring board 215 for each ultrasonic transducer 211. The wiring pattern connected to the transmission/reception circuitry 216a is electrically connected to the wiring pattern 215a. This electrically connects the transmission/reception circuitry 216a to the first electrode 211a and the second electrode 211b of each ultrasonic transducer 211.

The transmission/reception circuitry 216a transmits/receives various types of signals to/from each ultrasonic transducer 211. For example, upon receiving a driving signal transmitted from the apparatus main body 10, the transmission/reception circuitry 216a transmits the received driving signal to the ultrasonic transducer 211 as a driving target. This applies a voltage corresponding to the amplitude of the driving signal between the two electrodes (the first electrode 211a and the second electrode 211b) of the ultrasonic transducer 211 as the driving target. Applying the voltage between the two electrodes of the ultrasonic transducer 211 will drive the ultrasonic transducer 211 to emit ultrasonic waves.

Upon receiving reflected wave signals output from the plurality of ultrasonic transducers 211, the transmission/reception circuitry 216a applies a known bundling process to the received reflected wave signals and transmits the reflected wave signal obtained by the bundling process to the ultrasonic reception circuitry 12 of the apparatus main body 10.

The acoustic lens 217 focuses ultrasonic waves. The acoustic lens 217 is provided on a surface of the flexible wiring board 215 which is located in a direction in which ultrasonic waves are emitted.

Although FIGS. 2 and 3 exemplify the case in which the ultrasonic transducer unit is provided with the transmission/reception circuitry 216a, this is not exhaustive. The ultrasonic transducer unit may not be provided with the transmission/reception circuitry 216a and may be configured to supply driving signals transmitted from the ultrasonic transmission circuitry 11 of the apparatus main body 10 to the ultrasonic transducers 211.

The transmission/reception circuitry 216a may have the functions of the ultrasonic transmission circuitry 11 and the ultrasonic reception circuitry 12 of the apparatus main body 10. In this case, the ultrasonic transmission circuitry 11 and the ultrasonic reception circuitry 12 are omitted from the apparatus main body 10.

An operation of the ultrasonic diagnostic apparatus 1 having the above arrangement will be described next.

(Acquisition of Initial Data)

Figure 4:
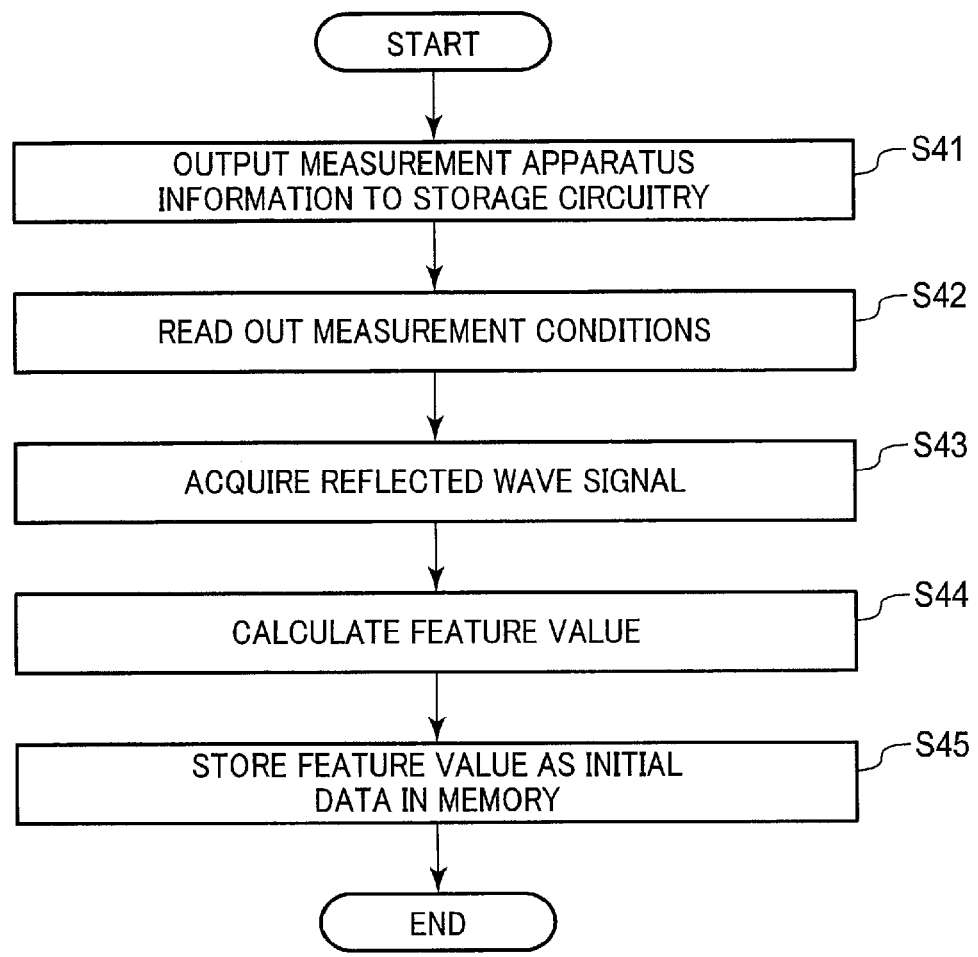
FIG. 4 is a flowchart when the control circuitry shown in FIG. 1 acquires initial data about the sensitivity of the ultrasonic probe.

FIG. 4 shows an example of a flowchart when the control circuitry 113 shown in FIG. 1 acquires initial data concerning the sensitivity of the ultrasonic probe 20.

First of all, the connector 23 of the ultrasonic probe 20 is connected to the apparatus main body 10 during a period from the manufacture of the ultrasonic diagnostic apparatus 1 to shipment. Note that at this time, the memory 24 of the ultrasonic probe 20 stores measurement condition information for measuring the sensitivity of the ultrasonic probe 20 for each channel. The manufacturer of the ultrasonic diagnostic apparatus 1 inputs, for example, an instruction to acquire initial data to the input interface 111. Upon receiving the instruction to acquire initial data, the control circuitry 113 of the ultrasonic diagnostic apparatus 1 executes the initial measurement function 1131. Upon executing the initial measurement function 1131, the control circuitry 113 reads out measurement apparatus information that can specify the apparatus main body 10 as a measurement apparatus from the internal memory 18 and causes the memory 24 of the ultrasonic probe 20 to store the information (step S41).

Subsequently, the control circuitry 113 reads out measurement condition information stored in the memory 24 of the ultrasonic probe 20 (step S42). The control circuitry 113 acquires a reflected wave signal for each channel based on the readout measurement condition information (step S43).

More specifically, the control circuitry 113 causes the ultrasonic transmission circuitry 11 to generate a driving voltage based on the measurement condition information, e.g., the driving voltage of the pulser circuitry of the ultrasonic transmission circuitry 11. At this time, the control circuitry 113 has set the applied waveform and driving frequency of a driving voltage in accordance with a feature value to be calculated. When the driving voltage generated by the ultrasonic transmission circuitry 11 is supplied to each ultrasonic transducer 211 via the transmission/reception circuitry 216a of the ultrasonic probe 20, the ultrasonic transducer 211 is driven to generate ultrasonic waves.

The generated ultrasonic waves are reflected by an interface SF between the surface of the acoustic lens 217 and air. The reflected ultrasonic waves reach the ultrasonic transducers 211 and respectively received by them. The ultrasonic transducers 211 output the received ultrasonic waves as reflected wave signals to the apparatus main body 10 via the transmission/reception circuitry 216a of the ultrasonic probe 20.

FIG. 5 is a schematic view showing an example of a reflected wave signal received by the apparatus main body 10 shown in FIG. 1. FIG. 5 shows a reflected wave signal when a driving signal with a driving frequency corresponding to the center frequency of the ultrasonic probe 20 is supplied to the ultrasonic transducer 211. A reflected wave signal is acquired for each channel. Each reflected wave signal includes a transmission waveform Wa, a multiple-reflected and unwanted vibration waveform Wb, a first reflected wave W1, and a second reflected wave W2. In this embodiment, the first reflected wave W1 represents a reflected wave at the first round trip of the ultrasonic wave between the ultrasonic transducer 211 and the interface SF. In the embodiment, the second reflected wave W2 represents a reflected wave at the second round trip of the ultrasonic wave between the ultrasonic transducer and the interface SF. As surface reflected waves for transmission/reception sensitivity measurement, the first reflected wave W1 or the second reflected wave W2 are used. Whether to use the first reflected wave W1 or the second reflected wave W2 is determined for each model of ultrasonic probe 20. An example of using the first reflected wave W1 will be described below.

The control circuitry 113 specifies the first reflected wave W1 based on a waveform acquisition interval T1 included in measurement condition information. The control circuitry 113 specifies the first reflected wave W1 by extracting a signal included in the waveform acquisition interval T1 from a reflected wave signal.

Note that the technique by which the control circuitry 113 acquires the first reflected wave W1 is not limited to the above technique. The control circuitry 113 may acquire the first reflected wave W1 by subtracting probe noise data included in measurement condition information from a reflected wave signal.

Upon acquiring the first reflected wave W1 in the reflected wave signal, the control circuitry 113 executes the calculation function 1133. Upon executing the calculation function 1133, the control circuitry 113 calculates a feature value based on the acquired first reflected wave W1 (step S44). For example, the control circuitry 113 calculates a sensitivity peak value as the feature value. More specifically, the control circuitry 113 obtains a maximum amplitude value (Vp-p) in the first reflected wave W1. The control circuitry 113 acquires a sensitivity peak value for each channel.

Figure 6:
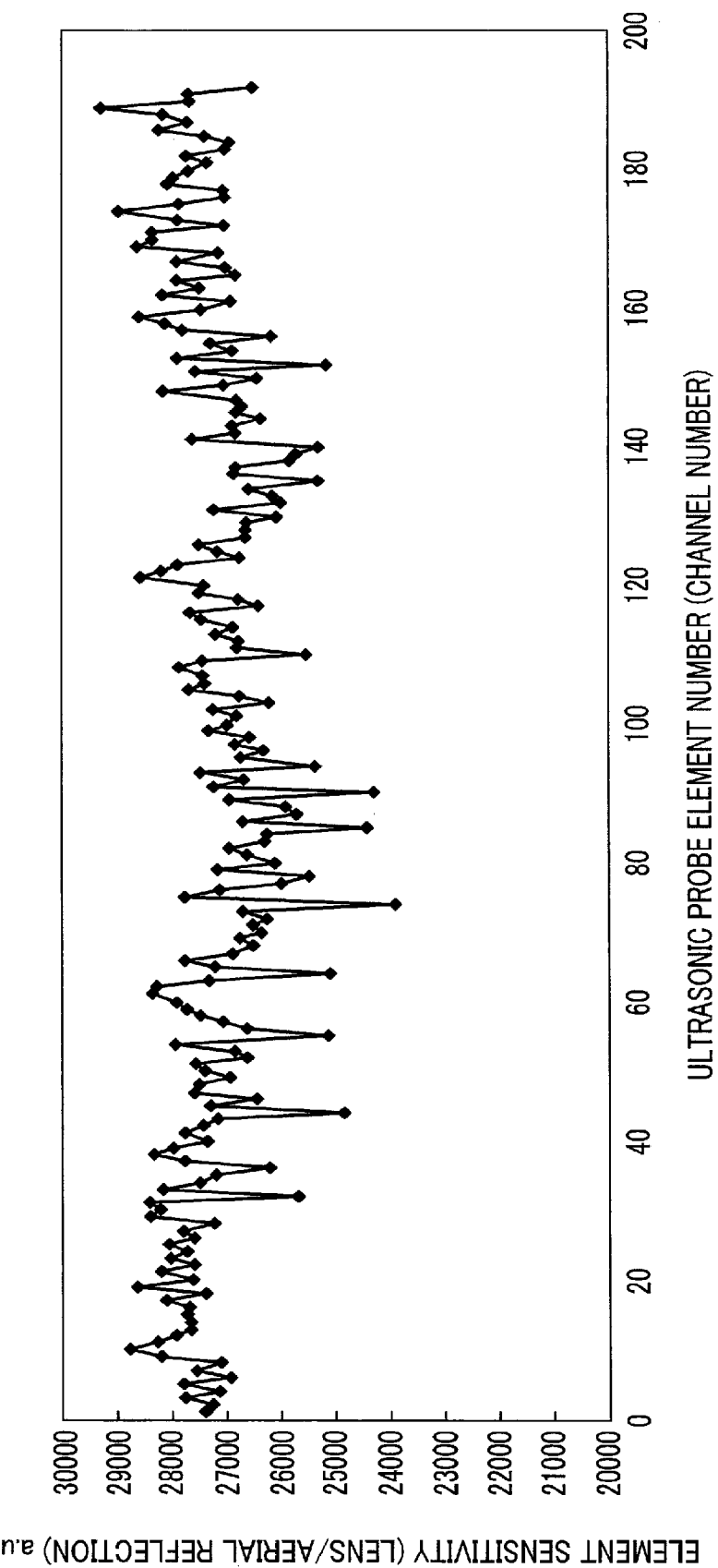
FIG. 6 is a graph representing a sensitivity peak value for each channel stored as initial data in the memory of the ultrasonic probe.

The control circuitry 113 stores the acquired sensitivity peak values as initial data in the memory 24 of the ultrasonic probe 20. The control circuitry 113 also stores the measurement date and time at the time of the measurement of the transmission/reception sensitivity of the ultrasonic probe 20, a temperature in the ultrasonic probe 20, and the like in addition to the measurement condition information stored in the memory 24 (step S45). The control circuitry 113 then terminates the processing. FIG. 6 is a graph showing an example of a sensitivity peak value for each channel stored as initial data in the memory 24.

(Management of Deterioration in Transmission/Reception Sensitivity of Ultrasonic Probe 20: Display)

Figure 7:
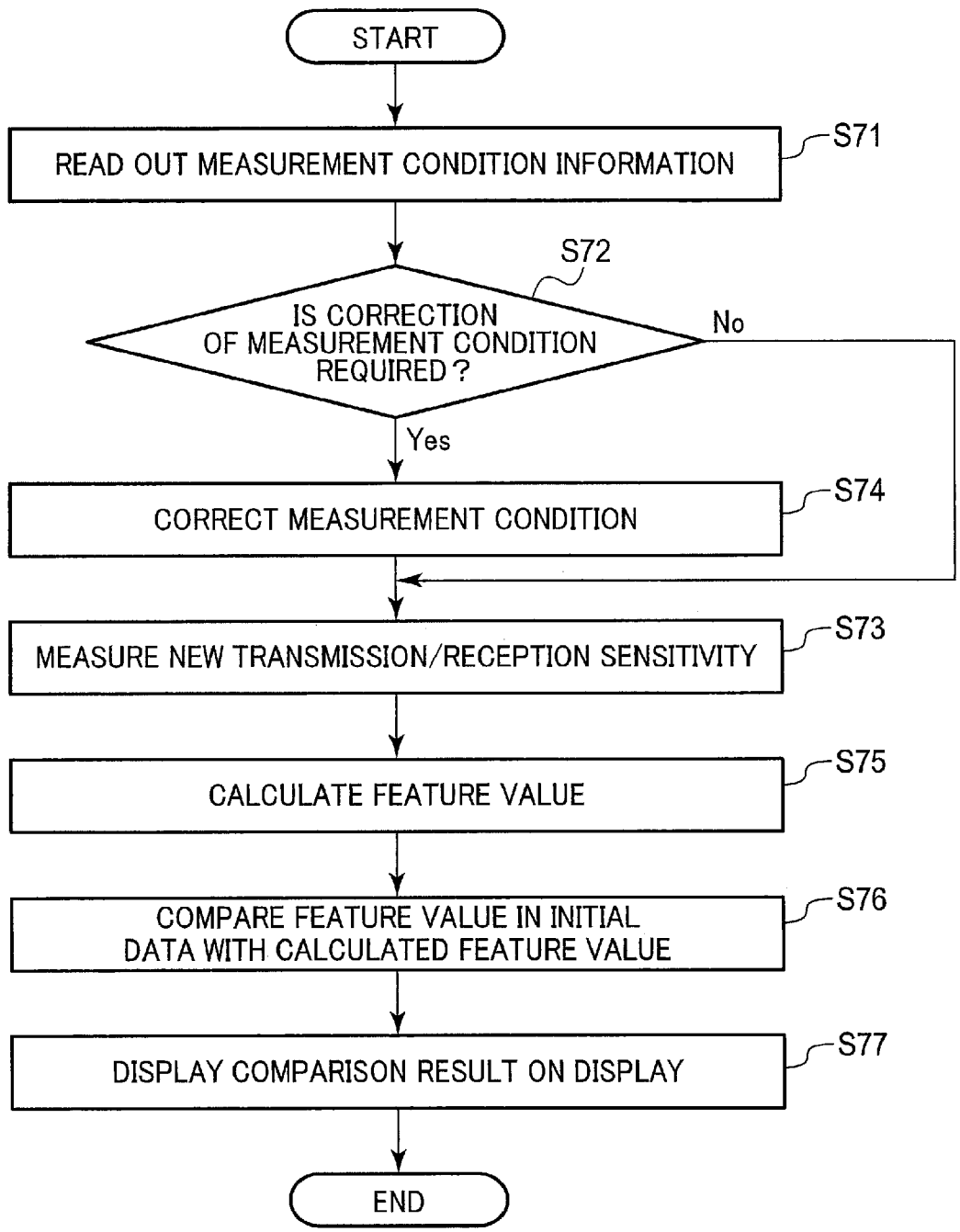
FIG. 7 is a flowchart when the control circuitry shown in FIG. 1 causes a display to display information concerning the sensitivity of the ultrasonic probe.

FIG. 7 shows an example of a flowchart when the control circuitry 113 shown in FIG. 1 causes the display 40 to display information concerning the sensitivity of the ultrasonic probe 20.

First of all, the control circuitry 113 executes the management measurement function 1132 at an arbitrary timing. The arbitrary timing includes the timing of the reception of an instruction signal input by the user or serviceman when he/she executes maintenance and inspection. The arbitrary timing may also be the time set in advance. For example, the arbitrary timing to be set is a timing other than when the ultrasonic probe 20 is used, such as late at night. The arbitrary timing may be a timing when the ultrasonic probe 20 is connected to the apparatus main body 10 or the timing of the reception of an instruction signal for remote measurement which is input by a serviceman via the network 100.

Upon executing the management measurement function 1132, the control circuitry 113 reads out measurement condition information stored in the memory 24 (step S71). The control circuitry 113 determines the necessity of the correction of the measurement condition stored in the memory 24 by collating the measurement apparatus information included in the readout measurement condition information with measurement apparatus information stored in the internal memory 18 of the apparatus main body 10 (step S72). A general technique may be used for this determination. For example, the control circuitry 113 determines whether to correct the measurement condition stored in the memory 24 in accordance with the output characteristics of the ultrasonic transmission circuitry 11 of the apparatus main body 10. Note that the collation of the measurement condition information included in the readout measurement condition information with the measurement apparatus information stored in the internal memory 18 is not essential.

If the correction of the measurement condition is not necessary (NO in step S72), the control circuitry 113 measures the transmission/reception sensitivity of the ultrasonic probe 20 in accordance with the readout measurement condition (step S73). More specifically, the control circuitry 113 causes the ultrasonic transmission circuitry 11 to generate a driving voltage based on, for example, a driving voltage and a driving frequency for the pulser circuitry of the ultrasonic transmission circuitry 11 stored in the measurement condition information. The control circuitry 113 receives reflected wave signals based on ultrasonic waves generated by the driving voltage and reflected by the interface SF between the surface of the acoustic lens 217 and air. The control circuitry 113 extracts desired signals from the reflected wave signals based on, for example, a waveform acquisition interval or probe noise data stored in the measurement condition information.

The channel whose transmission/reception sensitivity is measured in step S73 may be an arbitrary channel. For example, the control circuitry 113 may measure the transmission/reception sensitivity of all the channels. The control circuitry 113 may select a channel whose transmission/reception sensitivity is to be measured. In this case, the channel to be selected is a channel that greatly contributes to image quality. Measuring transmission sensitivity upon selecting a channel will shorten the measurement time of transmission/reception sensitivity.

If the correction of the measurement condition is necessary (YES in step S72), the control circuitry 113 corrects the readout measurement condition based on, for example, the output characteristics of the ultrasonic transmission circuitry 11 of the apparatus main body 10 (step S74). The process then advances to step S73.

Upon measuring transmission/reception sensitivity in step S73, the control circuitry 113 executes the calculation function 1133. Upon executing the calculation function 1133, the control circuitry 113 calculates the same type of feature values as that stored in the initial data based on the signals acquired in step S73 (step S75). For example, if sensitivity peak values are stored as feature values in the initial data, the control circuitry 113 calculates sensitivity peak values. The control circuitry 113 causes the memory 24 to store the calculated feature values and measurement condition information at the time of the acquisition of the feature values. In this case, the feature values and the measurement condition information stored in the memory 24 can be used for the evaluation measurement of the transmission/reception sensitivity of the ultrasonic probe 20 at a later time point. Note that the feature values in the initial data or feature values acquired at a predetermined time point after shipment may be used as a reference in evaluation measurement at the later time point.

Figure 8:
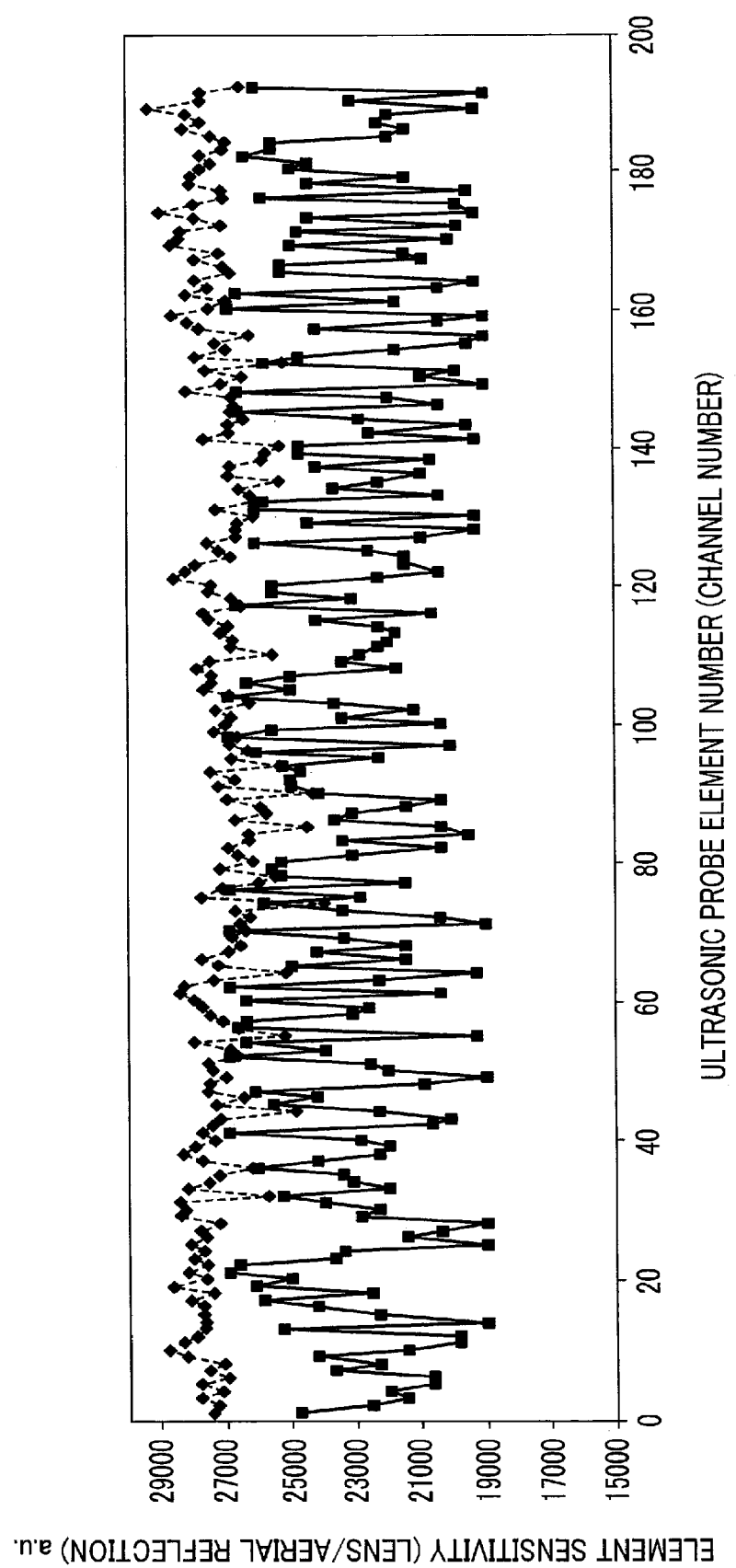
FIG. 8 is a graph representing the comparison between sensitivity peak values as initial data and each feature value acquired in sensitivity measurement.

The control circuitry 113 then executes the comparing function 1134. Upon executing the comparing function 1134, the control circuitry 113 reads out the initial data from the memory 24. The control circuitry 113 compares the readout feature values included in the initial data with the calculated feature values (step S76). FIG. 8 is a graph representing an example of comparison between sensitivity peak values as initial data and each feature value acquired in sensitivity measurement. Referring to FIG. 8, the broken line represents a sensitivity peak value for each channel as initial data, and the solid line represents a feature value for each channel which is acquired at a predetermined timing.

The control circuitry 113 may calculate an index value representing the difference between feature values by comparing the feature value included in the readout initial data with the calculated feature value. Examples of an index value representing the difference between feature values include a difference value and a change rate. FIG. 9 is a graph exemplarily showing the differences between sensitivity peak values as initial data and feature values acquired at predetermined timings.

Figure 10:
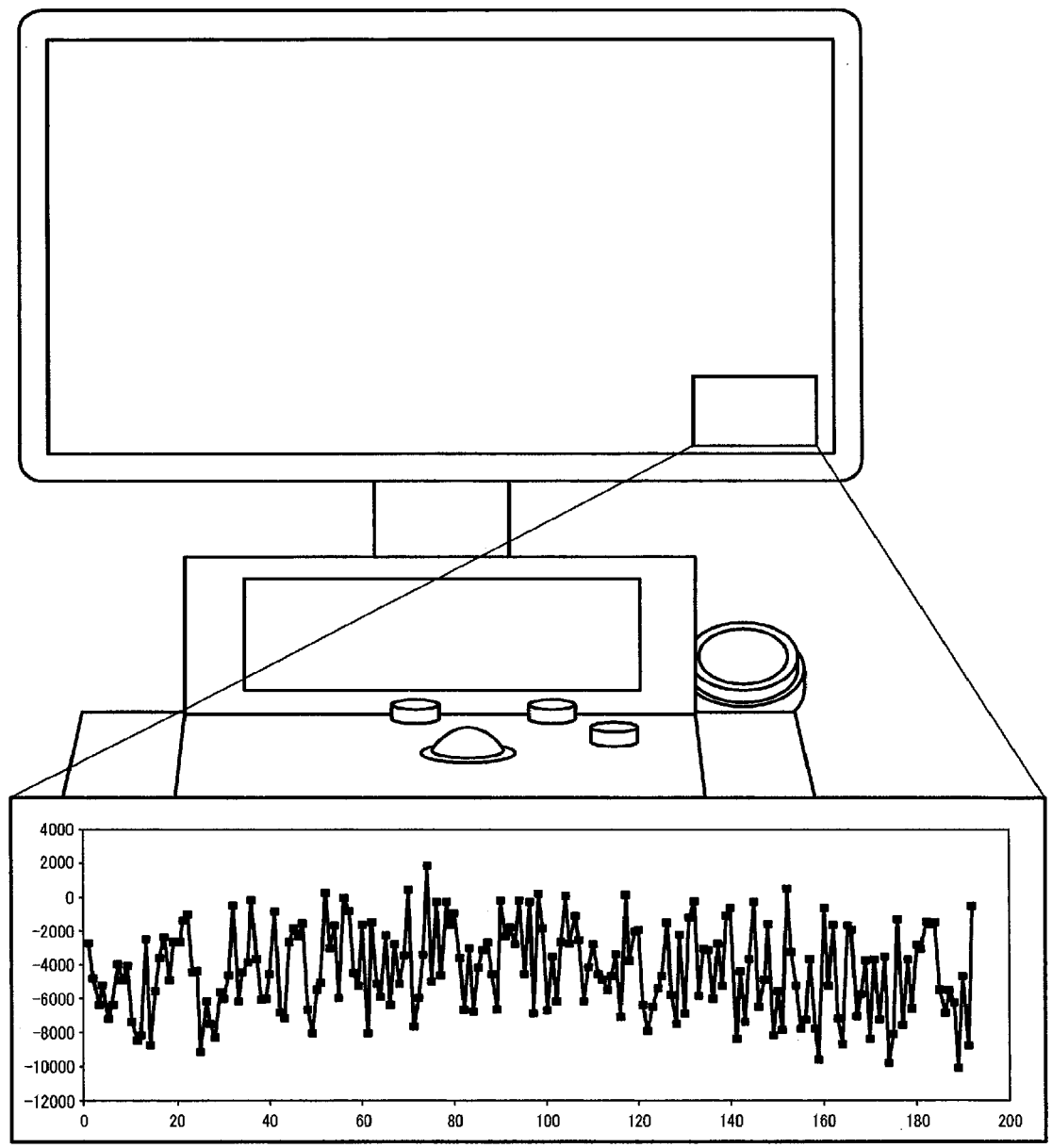
FIG. 10 is a view showing a display image on a display when displaying the differences shown in FIG. 9.

Upon comparing feature values included in the readout initial data with the calculated feature values, the control circuitry 113 executes the display control function 1135. Upon executing the display control function 1135, the control circuitry 113 controls the display processing circuitry 17 to cause the display 40 to display an image concerning the feature value comparison values (step S77). More specifically, for example, the control circuitry 113 generates image data for displaying the comparison results at a predetermined position on the display 40. The control circuitry 113 outputs the generated image data to the display processing circuitry 17, and causes the display 40 to display the image based on the image data. The comparison result displayed on the display 40 may be the visualization of temporal changes as shown in FIG. 8, i.e., feature values at two time points, or index values (differences, change rates, or the like) representing the differences between feature values. FIG. 10 is a view showing a display example on the display 40 when it displays the differences between the feature values shown in FIG. 9.

Note that the comparison result displayed on the display 40 is not limited to the comparison result between feature values at two time points, and may be the comparison result between feature values at a plurality of time points more than three time points. The control circuitry 113 reads out, for example, the feature values in the initial data and the feature values acquired at arbitrary time points after shipment from the memory 24. The control circuitry 113 compares the readout feature values with a calculated feature values.

The images displayed on the display 40 by the control circuitry 113 are not limited to comparison results. The control circuitry 113 may cause the display 40 to display the measurement conditions stored in the memory 24 together with the comparison result. In addition, the control circuitry 113 may cause the display 40 to display the use history of the ultrasonic probe 20 in the time interval from a past time point when sensitivity measurement was executed to the current time point together with the comparison result. The use history of the ultrasonic probe 20 is, for example, the history of driving times, modes, transmission outputs, temperatures, or the like, and is stored in, for example, the memory 24.

The control circuitry 113 may display the existence of the comparison result instead of the comparison result, generate image data representing an input icon for inputting a request to display the comparison result, and cause the display 40 to display an image based on the image data. Upon receiving a display request from the input icon via the input interface 111, the control circuitry 113 causes the display 40 to display an image representing the comparison result.

A technique of notifying outwardly at least one of the comparison result and the measurement condition is not limited to displaying on the display 40. The control circuitry 113 may output at least any one of the comparison result and the measurement condition to the external device 30 via the communication interface 112. In this case, the control circuitry 113 implements a communication control function 1137 by executing a program stored in the internal memory 18 and configured to manage the sensitivity of the ultrasonic probe 20. The communication control function 1137 is a function of outputting the feature value comparison result or the like to the external device 30.

For example, upon comparing the feature values included in the readout initial data with the calculated feature value, the control circuitry 113 executes the communication control function 1137. Upon executing the communication control function 1137, the control circuitry 113 controls the communication interface 112 to output data concerning the feature value comparison result or the like to the external device 30.

A flowchart when the control circuitry 113 causes the display 40 to display information concerning the sensitivity of the ultrasonic probe 20 is not limited to that shown in FIG. 7. For example, upon comparing the feature values included in the initial data read out from the memory 24 with the calculated feature values (step S76), the control circuitry 113 may determine whether the sensitivity of the ultrasonic probe 20 has deteriorated before the execution of the display control function 1135. At this time, the control circuitry 113 implements a determination function 1138 by executing a program stored in the internal memory 18 and configured to manage the sensitivity of the ultrasonic probe 20. The determination function 1138 is a function of determining whether the sensitivity of the ultrasonic probe 20 has deteriorated.

For example, upon comparing the feature values included in the readout initial data with the calculated feature values, the control circuitry 113 executes the determination function 1138. Upon executing the determination function 1138, the control circuitry 113 determines whether the sensitivity of the ultrasonic probe 20 has deteriorated, based on the feature value comparison result.

More specifically, for example, the control circuitry 113 determines whether the sensitivity of the ultrasonic probe 20 has deteriorated by determining whether index values (difference, change rate, or the like) representing the differences between the feature values included in the readout initial data and the calculated feature values satisfies a predetermined requirement. For example, if the index values represent differences, the control circuitry 113 determines whether the number of channels in each of which the difference between feature values is equal to or more than a preset value is equal to or more than a predetermined number. If the index values represent change rates, the control circuitry 113 also determines whether the number of channels in each of which the change rate is equal to or more than a preset value is equal to or more than a predetermined number.

For example, the control circuitry 113 may also determine whether the sensitivity of the ultrasonic probe 20 has deteriorated by determining whether the difference between a reference value acquired based on the feature values included in the readout initial data and the calculated feature values satisfies a predetermined requirement. In this case, the reference value acquired based on the feature values is, for example, the average value, median value, minimum value, or maximum value of the feature values. The control circuitry 113 determines whether the number of channels in each of which the difference between a reference value and a calculated feature value is equal to or more than a preset value is equal to or more than a predetermined number.

Upon determining that the sensitivity of the ultrasonic probe 20 has deteriorated, the control circuitry 113 executes the display control function 1135. Upon determining that the sensitivity of the ultrasonic probe 20 has not deteriorated, for example, the control circuitry 113 does not execute the display control function 1135, and hence displays no comparison result.

(Management of Deterioration in Transmission/Reception Sensitivity of Ultrasonic Probe 20: Correction)

Figure 11:
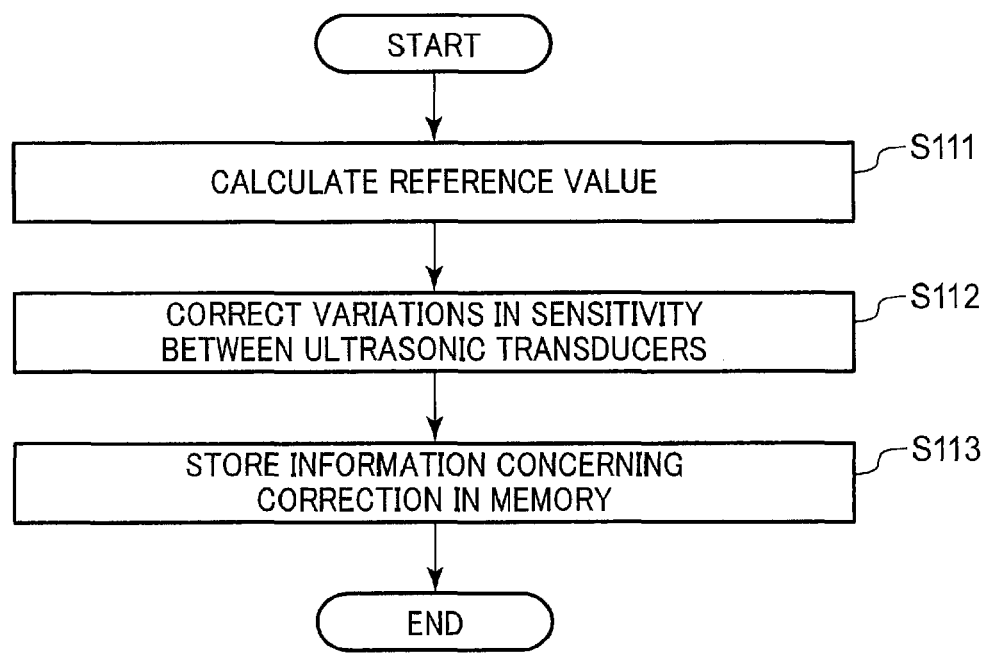
FIG. 11 is a flowchart when the control circuitry shown in FIG. 1 corrects the sensitivity of the ultrasonic probe.

FIG. 11 shows an example of a flowchart when the control circuitry 113 shown in FIG. 1 corrects the sensitivity of the ultrasonic probe 20.

As indicated by step S76 in FIG. 7, upon comparing the feature values included in the initial data with the calculated feature values, the control circuitry 113 executes the correction processing function 1136. Upon executing the correction processing function 1136, the control circuitry 113 executes, based on the feature value comparison result, the processing for correcting variations in sensitivity between the ultrasonic transducers 211 provided for the ultrasonic probe 20.

More specifically, the control circuitry 113 calculates a reference value from the feature values included in the initial data read out from the memory 24 (step S111). In this case, the calculated reference value is, for example, the average value, median value, minimum value, or maximum value of feature values. Note that if the feature values are center frequencies or the like, the reference value is, for example, an average spectrum or specific frequency.

The control circuitry 113 corrects variations in sensitivity between the ultrasonic transducers 211 so as to make the feature values obtained by the measurement almost coincide with the calculated reference value (step S112).

Then control circuitry 113 stores information after correction in the measurement condition information stored in the memory 24 (step S113), and terminates the processing. More specifically, for example, the control circuitry 113 changes the driving voltage of the pulser circuitry of the ultrasonic transmission circuitry 11 for each channel based on the reference value, and stores the changed value concerning the driving voltage of the pulser circuitry in the measurement condition information stored in the memory 24.

Figure 12:
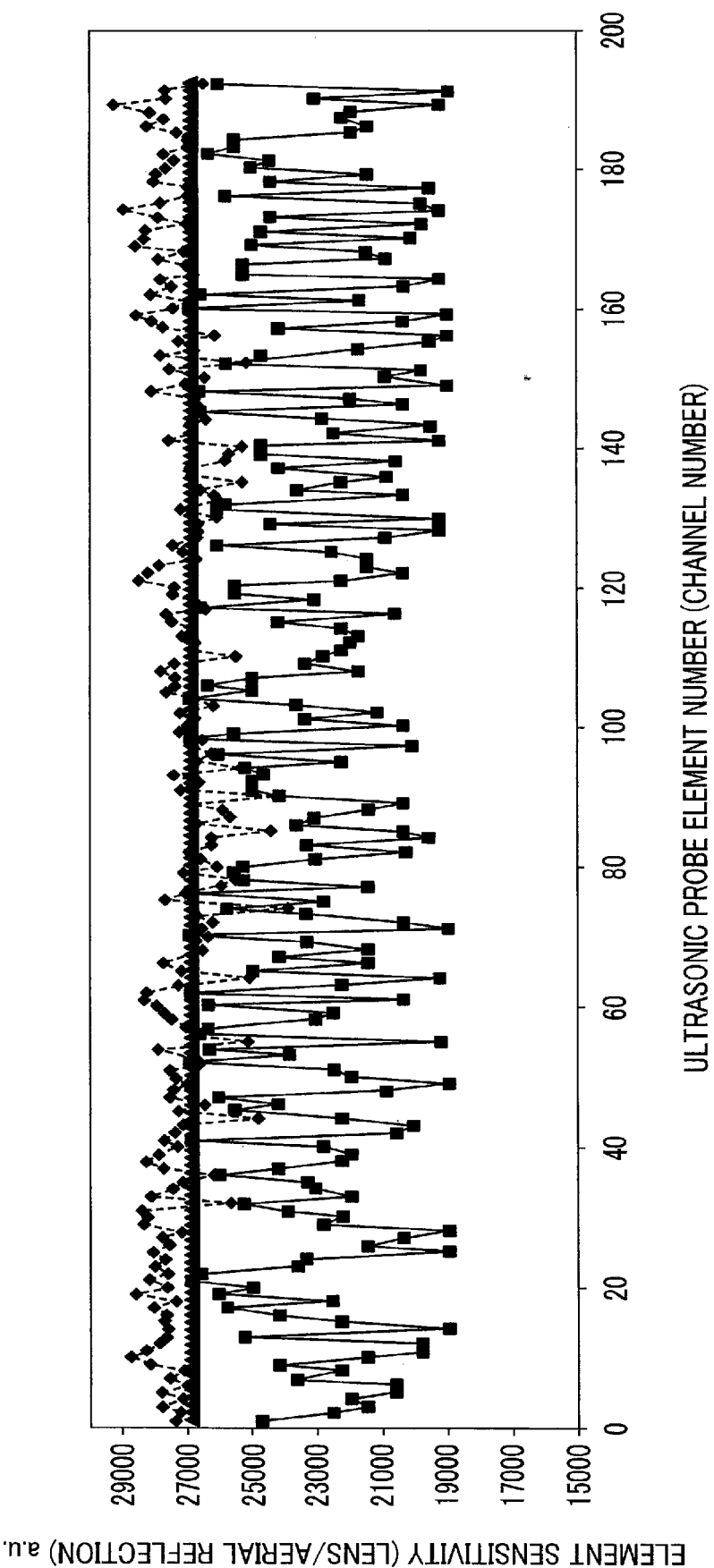
FIG. 12 is a graph representing the sensitivity of the ultrasonic probe corrected based on the comparison shown in FIG. 8.

FIG. 12 is a graph showing an example of the sensitivity of the ultrasonic probe 20 corrected in the comparative example shown in FIG. 8. Referring to FIG. 12, the broken line represents a sensitivity peak value for each channel as initial data, the solid line represents a feature value for each channel which is acquired at a predetermined timing, and the thick line represents a sensitivity peak value for each channel after the correction of the sensitivity.

Note that a flowchart when the control circuitry 113 corrects the sensitivity of the ultrasonic probe 20 is not limited to that shown in FIG. 11. For example, upon comparing the feature values included in the initial data read out from the memory 24 with the calculated feature values (step S76), the control circuitry 113 may determine whether the sensitivity of the ultrasonic probe 20 has deteriorated, i.e., correction processing needs to be executed, before the execution of the correction processing function 1136.

Figure 13:
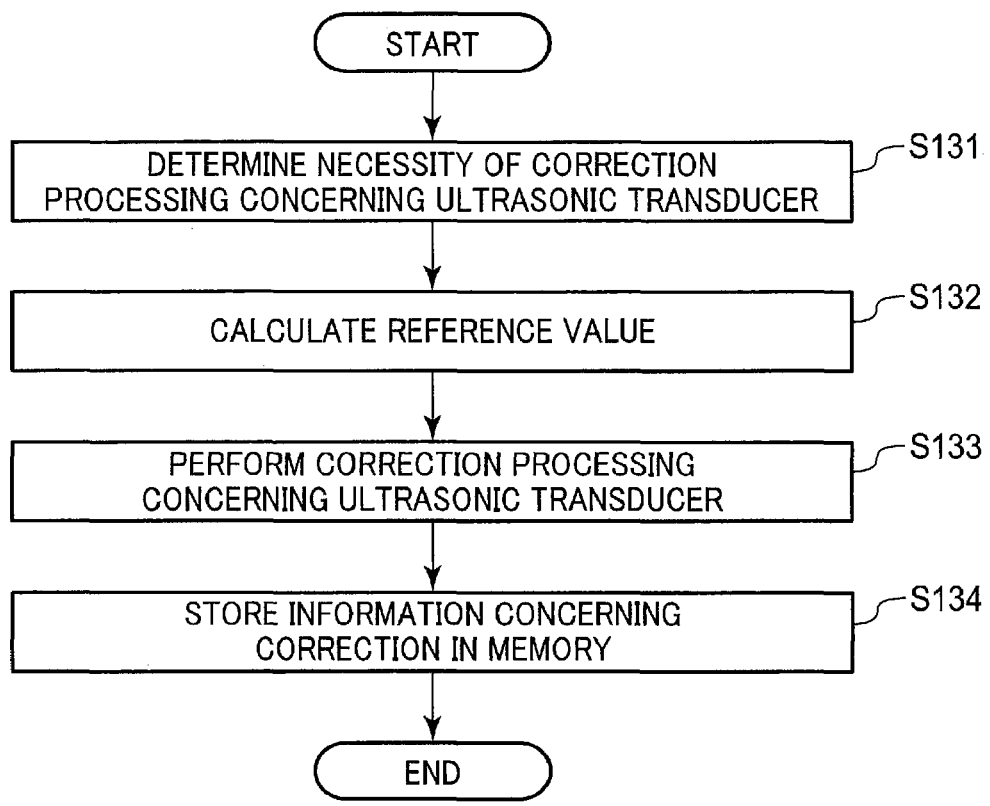
FIG. 13 is another flowchart when the control circuitry shown in FIG. 1 corrects the sensitivity of the ultrasonic probe.

FIG. 13 is another flowchart when the control circuitry 113 shown in FIG. 1 corrects the sensitivity of the ultrasonic probe 20.

As indicated by step S76 in FIG. 7, upon comparing the feature values included in the initial data with the calculated feature values, the control circuitry 113 executes the determination function 1138. Upon executing the determination function 1138, the control circuitry 113 determines the necessity of correction processing about each ultrasonic transducer 211 based on the feature value comparison result (step S131).

More specifically, the control circuitry 113 determines the necessity of correction processing for each ultrasonic transducer 211 by determining whether index values (difference, change rate, or the like) representing the differences between the feature values included in the readout initial data and the calculated feature values satisfies a predetermined requirement. For example, if the index value represents a difference and the difference between the feature values is equal to or more than a preset value, the control circuitry 113 determines that correction processing needs to be executed for the ultrasonic transducer 211. In addition, if the index value represents a change rate, the control circuitry 113 determines that correction processing needs to be executed for the ultrasonic transducer 211 whose change rate is equal to or more than a preset value.

For example, the control circuitry 113 may calculate reference values based on the feature values included in the readout initial data and determine the necessity of correction processing for each ultrasonic transducer 211 by determining whether the differences between the calculated reference values and the calculated feature values satisfies a predetermined requirement. For example, if the difference between the reference value and the calculated feature value is equal to or more than a preset value, the control circuitry 113 determines that correction processing needs to be executed for the ultrasonic transducer 211.

Upon determining that there is any ultrasonic transducer 211 requiring correction processing, the control circuitry 113 executes the correction processing function 1136.

More specifically, the control circuitry 113 calculates a reference value from the feature values included in the initial data read out from the memory 24 (step S132). Note that if the reference value has already been calculated in step S131, step S132 is not necessary. The control circuitry 113 executes correction processing for, for example, making feature values to be obtained by measurement almost coincide with the calculated reference value with respect to the ultrasonic transducer 211 for which the control circuitry 113 determines that correction processing is necessary (step S133). The control circuitry 113 stores information after the correction in the measurement condition information stored in the memory 24 (step S134), and terminates the processing. More specifically, the control circuitry 113 changes, based on the reference value, the driving voltage supplied to the ultrasonic transducer 211 for which the control circuitry 113 determines that correction processing is necessary, and stores the value obtained by changing the driving voltage in the measurement condition information stored in the memory 24.

Note that in step S132, for example, the control circuitry 113 may calculate the reference value based on the feature values calculated by the calculation function 1133. For example, the control circuitry 113 may set the average value, median value, minimum value, maximum value, or the like of calculated feature values as the reference value. If the feature value is a center frequency or the like, the reference value is, for example, an average spectrum or specific frequency.

The control circuitry 113 may also calculate the reference value based on the minimum value of the calculated feature values. For example, the control circuitry 113 increases the driving voltages supplied to the ultrasonic transducers 211 stepwise a plurality of times, and calculates feature values every time increasing the driving voltages. At this time, the feature values calculated for the ultrasonic transducers 211 that have deteriorated do not return to the initial feature values even after an increase in driving voltages, but returns to only predetermined feature values smaller than the initial feature values. The control circuitry 113 sets, for example, as a reference value, the minimum value of the feature values calculated with respect to the ultrasonic transducers 211 whose driving voltages are increased.

The processing for correcting variations in sensitivity between the ultrasonic transducers 211 is not limited to correction based on a reference value. For example, the control circuitry 113 may correct variations in sensitivity between the ultrasonic transducers 211 through re-polarization of the ultrasonic transducers 211.

FIG. 14 shows an example of a flowchart when the control circuitry 113 shown in FIG. 1 corrects the sensitivity of the ultrasonic probe 20 through re-polarization of the ultrasonic transducers 211.

As indicated by step S76 in FIG. 7, upon comparing the feature values included in the initial data with the calculated feature values, the control circuitry 113 executes the determination function 1138. Upon executing the determination function 1138, the control circuitry 113 determines the necessity of re-polarization of the ultrasonic transducer 211 based on the feature value comparison result (step S141). At this time, if the control circuitry 113 determines the necessity of re-polarization based on an index value, for example, a threshold concerning the index value is larger than the threshold in step S131. If the control circuitry 113 determines the necessity of re-polarization based on a reference value calculated from the feature values included in the initial data, for example, a threshold concerning the differences between the reference value and the feature values is larger than the threshold in step S131.

Upon determining that there is any ultrasonic transducer 211 requiring re-polarization, the control circuitry 113 executes a correction processing function 116. Upon executing the correction processing function 116, the control circuitry 113 re-polarizes the ultrasonic transducer 211 for which the control circuitry 113 determines that re-polarization is necessary (step S142). More specifically, the control circuitry 113 loads, for a preset period, for example, a DC or AC voltage having a preset magnitude to the ultrasonic transducer 211 for which the control circuitry 113 determines that re-polarization is necessary.

Subsequently, the control circuitry 113 measures the transmission/reception sensitivity of the ultrasonic probe 20 after re-polarization based on the measurement condition information read out in advance (step S73). Upon measuring the transmission/reception sensitivity, the control circuitry 113 executes the calculation function 1133 to calculate feature values based on signals acquired by the measurement (step S75).

The control circuitry 113 then executes the comparing function 1134 to compare feature values included in the initial data with the calculated feature values (step S76). Upon comparing the feature values, the control circuitry 113 executes the correction processing function 1136 to execute the processing for correcting variations in sensitivity between the ultrasonic transducers 211 provided for the ultrasonic probe 20 based on the feature value comparison result (steps S111 to S113), and terminates the processing.

Note that a flowchart when the control circuitry 113 corrects the sensitivity of the ultrasonic probe 20 through re-polarization of the ultrasonic transducer 211 is not limited to that shown in FIG. 14. For example, upon comparing the feature values included in the initial data read out from the memory 24 with the calculated feature values (step S76), the control circuitry 113 may determine whether correction processing needs to be executed for the ultrasonic transducers 211 before the execution of the correction processing function 1136.

Note that FIGS. 11, 13, and 14 each have exemplified the case in which variations in sensitivity between the ultrasonic transducers 211 are corrected by using a reference value based on feature values included in the initial data. However, the feature values used to calculate the reference value are not limited to that included in the initial data. For example, the control circuitry 113 compares feature values acquired at a predetermined time point after shipment with the calculated feature values. The control circuitry 113 may then calculate a reference value based on the feature values acquired at the predetermined time point after shipment.

As described above, in the first embodiment, the control circuitry 113 of the ultrasonic diagnostic apparatus 1 stores information concerning reflected wave signals in the memory 24 of the ultrasonic probe 20 at a first time point as the manufacture/shipment time or a predetermined time point after the manufacture/shipment. The information concerning the reflected wave signals includes, for example, feature values concerning the transmission/reception sensitivity of the ultrasonic probe 20 and measurement conditions at the time of the acquisition of the feature values. The control circuitry 113 acquires feature values concerning the transmission/reception sensitivity of the ultrasonic probe 20 based on the measurement conditions stored in the memory 24 at an arbitrary timing (second time point) after the first time point. The control circuitry 113 then notifies the user of the comparison result between the initial feature values stored in the memory 24 and the newly acquired feature values. This makes it possible for the ultrasonic diagnostic apparatus 1 to notify the user of a change in the transmission/reception sensitivity of the ultrasonic probe 20 after the lapse of a predetermined period since shipment. In addition, there is no need to change the current configuration, and hence there is no limitation on acoustic characteristics. In addition, there is no increase in cost due to a design change.

In the first embodiment, the control circuitry 113 also determines whether the sensitivity of the ultrasonic probe 20 has deteriorated. If the sensitivity of the ultrasonic probe 20 has deteriorated, the control circuitry 113 notifies the user of the comparison result between initial feature values and newly acquired feature values. With this operation, the control circuitry 113 notifies the user of the comparison result only when the transmission/reception sensitivity of the ultrasonic probe 20 has deteriorated. This allows the user to intuitively recognize that the transmission/reception sensitivity of the ultrasonic probe 20 has deteriorated.

In the first embodiment, the control circuitry 113 performs correction to suppress variations in sensitivity between the ultrasonic transducers 211 provided for the ultrasonic probe 20 based on a feature value comparison result. This makes it possible to suppress variations in sensitivity between the ultrasonic transducers 211 while recovering the sensitivity of the ultrasonic probe 20 to a sensitivity almost equal to the sensitivity regarded as a reference.

In the first embodiment, the control circuitry 113 compares feature values acquired at two time points to determine whether correction processing is necessary for the ultrasonic transducer 211. If the correction processing is necessary, the control circuitry 113 corrects variations in sensitivity between the ultrasonic transducers 211. This makes it possible to correct variations in sensitivity between the ultrasonic transducers 211 with respect to the ultrasonic probe 20 whose transmission/reception sensitivity has deteriorated in the time interval from the first time point to the second time point, thereby suppressing a processing load on the control circuitry 113.

The first embodiment has exemplified the case in which the control circuitry 113 causes the memory 24 to store feature values acquired at the manufacture/shipment time of the ultrasonic diagnostic apparatus 1 or a predetermined time point after the manufacture/shipment. The data stored in the memory 24 at the manufacture/shipment time of the ultrasonic diagnostic apparatus 1 or a predetermined time point after the manufacture/shipment is not limited to the feature values. The control circuitry 113 may cause the memory 24 to store waveform information of reflected wave signals instead of the feature values. That is, information concerning the reflected wave signals may include waveform information instead of the feature values.

Figure 15:
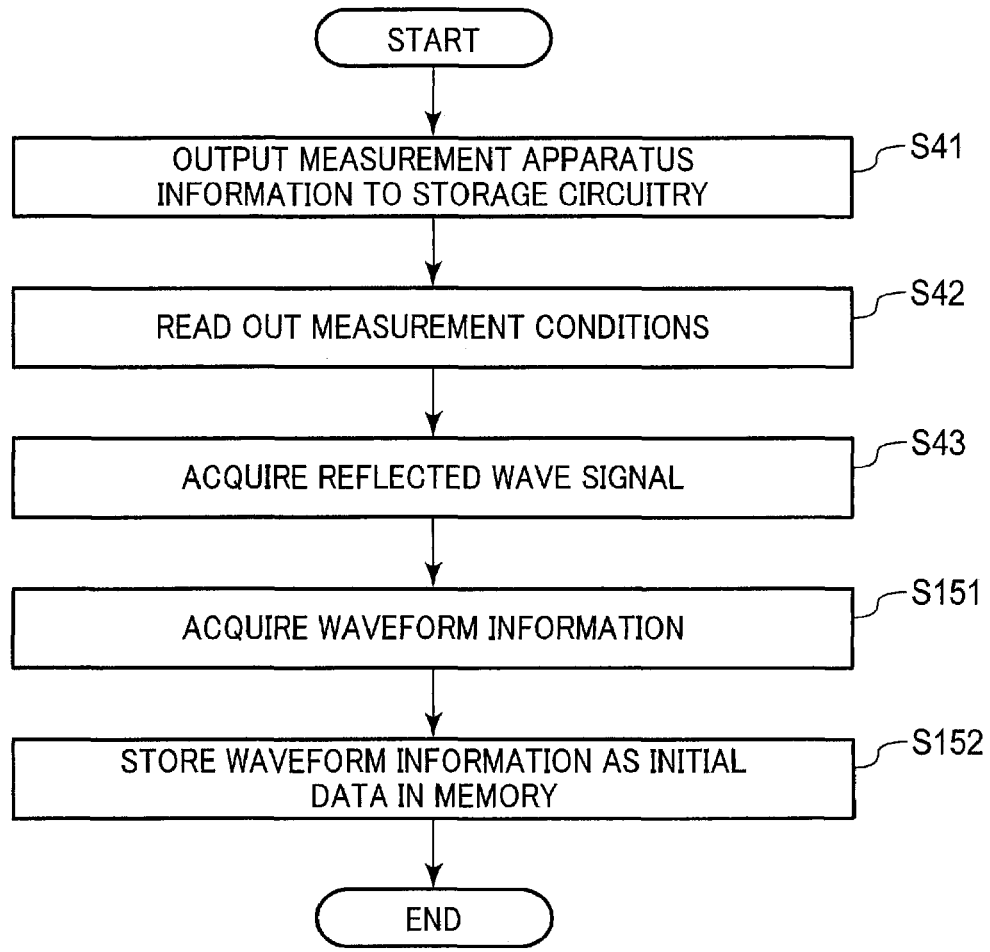
FIG. 15 is a flowchart when the control circuitry shown in FIG. 1 stores waveform information as initial data.

FIG. 15 shows an example of a flowchart when the control circuitry 113 shown in FIG. 1 stores waveform information as initial data.

The control circuitry 113 of the ultrasonic diagnostic apparatus 1 acquires a reflected wave signal for each channel of the ultrasonic probe 20 by executing steps S41 to S43 shown in FIG. 4. The control circuitry 113 acquires waveform information concerning the acquired reflected wave signals (step S151), and stores the acquired waveform information as initial data in the memory 24. The control circuitry 113 also stores measurement date and time when the waveform information is acquired, a temperature in the ultrasonic probe 20, and the like in addition to the measurement condition information stored in the memory 24 (step S152). Note that the control circuitry 113 may extract desired signals from reflected wave signals and acquire waveform information concerning the extracted signals.

FIG. 16 shows another example of the flowchart when the control circuitry 113 shown in FIG. 1 causes the display 40 to display information concerning the sensitivity of the ultrasonic probe 20.

Upon determining in step S72 that the correction of measurement conditions is not necessary, the control circuitry 113 reads out the waveform information as initial data from the memory 24 and executes the calculation function 1133. Upon executing the calculation function 1133, the control circuitry 113 calculates feature values based on the readout waveform information (step S161).

Upon calculating feature values, the control circuitry 113 acquires reflected wave signals by measuring the transmission/reception sensitivity of the ultrasonic probe 20 in accordance with the measurement conditions read out from the memory 24 (step S73). The control circuitry 113 acquires waveform information concerning the acquired reflected wave signals (step S162). The control circuitry 113 causes the memory 24 to store the acquired waveform information and measurement condition information at the time of the measurement of the transmission/reception sensitivity of the ultrasonic probe 20. In this case, the waveform information and the measurement condition information stored in the memory 24 may be used to measure the transmission/reception sensitivity information of the ultrasonic probe 20 at a later time point.

Upon calculating feature values based on the acquired waveform information in step S75, the control circuitry 113 causes the display 40 to display a feature value comparison result through the processing in steps S76 and S77.

As described above, storing waveform information in the memory 24 in advance makes it possible to calculate feature values based on the waveform information at an arbitrary timing.

Note that in case where the waveform information is stored in the memory 24, the information display on the display 40 is not limited to feature value comparison results. The control circuitry 113 may display, on the display 40, the comparison result between waveform information at a predetermined time point and waveform information of reflected wave signals received at an arbitrary timing.

The first embodiment has exemplified the case in which initial data and measurement condition information are stored in the memory 24. The information stored in the memory 24 is not limited to them. Various types of values set as manufacture/shipment references may be stored in the memory 24. The various types of values include, for example, a sensitivity peak value, center frequency, wave train length, and fractional bandwidth.

In case where a value set based on the manufacture/shipment reference is stored in the memory 24, the control circuitry 113 compares, for example, the value set based on the manufacture/shipment reference with feature values obtained by measurement by using the comparing function 1134.

In case where a value set based on the manufacture/shipment reference is stored in the memory 24, the control circuitry 113 may cause the display 40 to display, for example, the comparison result between the value set based on the manufacture/shipment reference and feature values by using the display control function 135. In addition, when the control circuitry 113 acquires a deterioration tendency of the sensitivity of the ultrasonic probe 20 and maintains the deterioration tendency, the control circuitry 113 may cause the display 40 to display the time when the acquired feature value does not reach the value set in advance based on the manufacture/shipment reference.

In case where a value set based on the manufacture/shipment reference is stored in the memory 24, the control circuitry 113 executes the correction processing function 1136 to correct the sensitivity of the ultrasonic probe 20 so as to make feature values to be acquired become the value set based on the manufacture/shipment reference. Note that the control circuitry 113 may correct the sensitivity of the ultrasonic probe 20 so as to set the maximum output allowed according to the laws and regulations.

In case where a value set based on the manufacture/shipment reference is stored in the memory 24, the control circuitry 113 may determine whether the sensitivity of the ultrasonic probe 20 has deteriorated, based on the comparison result between the value set based on the manufacture/shipment reference and the acquired feature values by using the determination function 1138.

The first embodiment has exemplified the case in which the memory 24 is provided in either the probe head 21 of the ultrasonic probe 20 or the connector 23. However, this is not exhaustive. The ultrasonic probe 20 may not be provided with the memory 24, and initial data, measurement condition information, and the like may be stored in memory provided in the external device 30. In addition, initial data, measurement condition information, and the like may be stored in the internal memory 18 provided in the apparatus main body 10.

(Modification)

Figure 17:
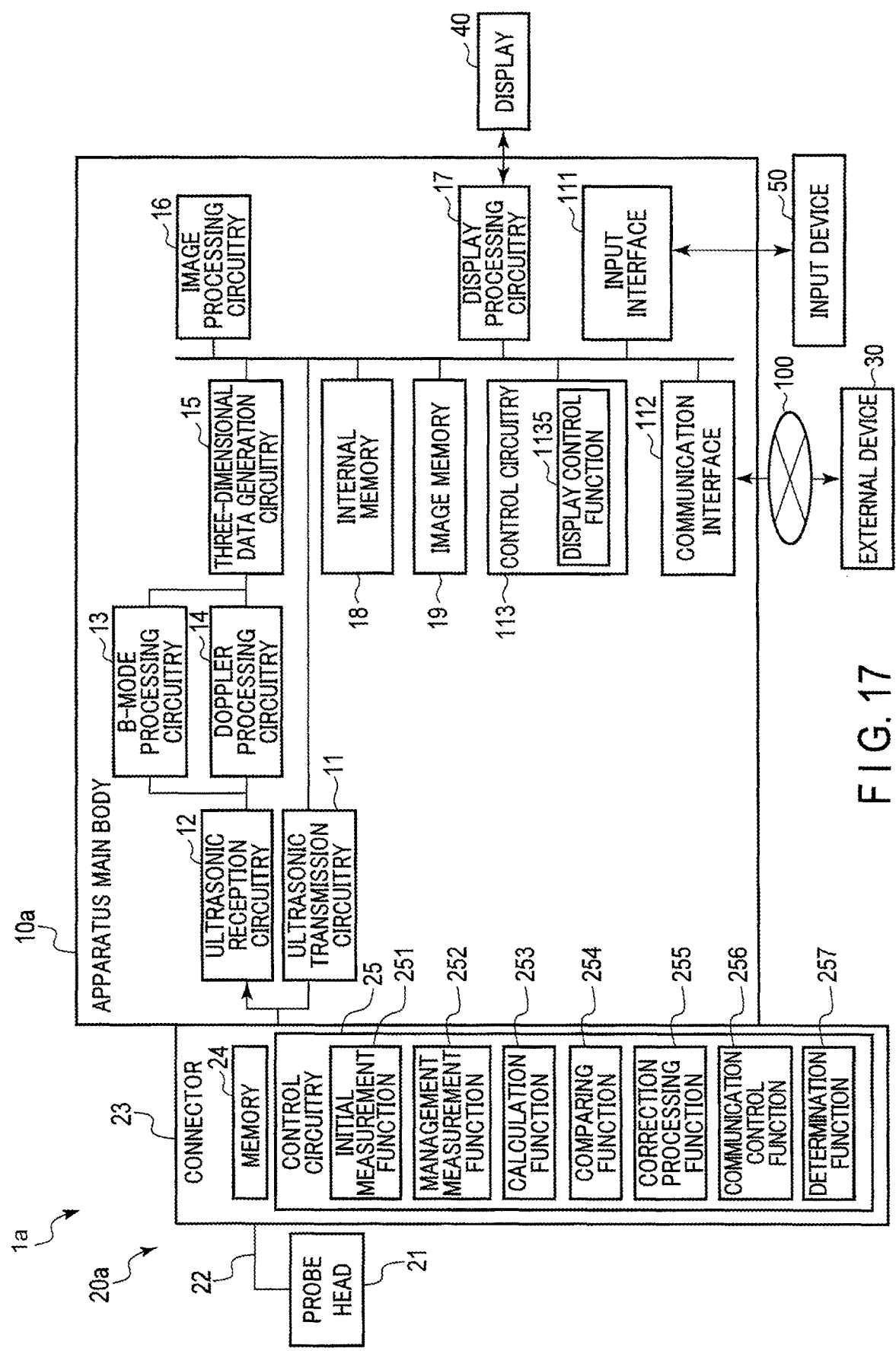
FIG. 17 is a block diagram showing another arrangement of the ultrasonic diagnostic apparatus according to the first embodiment.

The first embodiment has exemplified the case in which the control circuitry 113 of the apparatus main body 10 executes a program for managing the sensitivity of the ultrasonic probe 20. However, this is not exhaustive. Control circuitry 25 of an ultrasonic probe 20a may execute the program for managing the sensitivity of the ultrasonic probe 20. FIG. 17 is a block diagram showing an example of the arrangement of an ultrasonic diagnostic apparatus 1a according to the first embodiment. The control circuitry 25 executes the program for managing the sensitivity of the ultrasonic probe 20, which is stored in the internal memory 18, to implement a function corresponding to the program. The control circuitry 25 may include, for example, an initial measurement function 251, a management measurement function 252, a calculation function 253, a comparing function 254, and a correction processing function 255. The control circuitry 25 may also include a communication control function 256 and a determination function 257.

The initial measurement function 251 is a function of acquiring initial data concerning the ultrasonic probe 20. Upon executing the initial measurement function 251, the control circuitry 25 reads out, for example, measurement condition information stored in the memory 24 at the time of the manufacture of the ultrasonic probe 20. The control circuitry 25 controls the transmission/reception circuitry 216a based on the readout measurement condition information. The control circuitry 25 acquires a reflected wave signal for each channel under the setting of the acquired measurement conditions. The control circuitry 25 stores, in the memory 24, measurement condition information at the time of the measurement of reflected wave signals and initial data based on the reflected wave signals.

The management measurement function 252 is a function of measuring the sensitivity of the ultrasonic probe 20. Upon executing the management measurement function 252, the control circuitry 25 controls the transmission/reception circuitry 216a based on measurement condition information stored in the memory 24 of the ultrasonic probe 20. The control circuitry 25 acquires a reflected wave signal for each channel under the setting of measurement conditions.

The calculation function 253 is a function of calculating feature values based on acquired reflected wave signals. Upon executing the calculation function 253, the control circuitry 25 calculates a feature value by analyzing the reflected wave system of the acquired reflected wave signal.

The comparing function 254 is a function of comparing the feature values acquired at two different time points. Upon executing the comparing function 254, the control circuitry 25 compares feature values included in the initial data stored in the memory 24 with feature values obtained by measurement. A comparison result is output to the apparatus main body 10 and displayed on the display 40 by the control circuitry 113 of the apparatus main body 10.

The correction processing function 255 is a function of correcting variations in sensitivity between the ultrasonic transducers 211 of the ultrasonic probe 20. Upon executing the correction processing function 255, the control circuitry 25 corrects variations in sensitivity between the ultrasonic transducers 211 provided for the ultrasonic probe 20 based on a feature value comparison result. For example, the control circuitry 25 changes the driving voltage of the transmission/reception circuitry 216a so as to make the feature values to be obtained by measurement satisfy a requirement concerning a predetermined reference value. The control circuitry 25 stores the driving voltage of the transmission/reception circuitry 216a after the change in the measurement condition information stored in the memory 24.

Note that the processing for correcting variations in sensitivity between the ultrasonic transducers 211 is not limited to changing the driving voltage of the transmission/reception circuitry 216a. The control circuitry 25 may change the gain of the transmission/reception circuitry 216a based on a reference value.

The control circuitry 25 re-polarizes the ultrasonic transducer 211 by loading, for a preset period, a DC or AC voltage having a predetermined magnitude from the transmission/reception circuitry 216a to the ultrasonic transducer 211.

The communication control function 256 is a function of outputting a feature value comparison result and the like to the external device 30. Upon executing the communication control function 256, the control circuitry 25 outputs data concerning a feature value comparison result or the like to the external device 30 by, for example, radio.

The determination function 257 is a function of determining whether the sensitivity of the ultrasonic probe 20 has deteriorated. Upon executing the determination function 257, the control circuitry 25 determines, based on a feature value comparison result, whether the sensitivity of the ultrasonic probe 20 has deteriorated.

Second Embodiment

The first embodiment has exemplified the case in which the control circuitry 113 and 25 of the ultrasonic diagnostic apparatus 1 execute the program for managing the sensitivity of the ultrasonic probe 20. The second embodiment will exemplify a case in which, for example, control circuitry 65 of a management apparatus 60 held by a serviceman executes this program.

Figure 18:
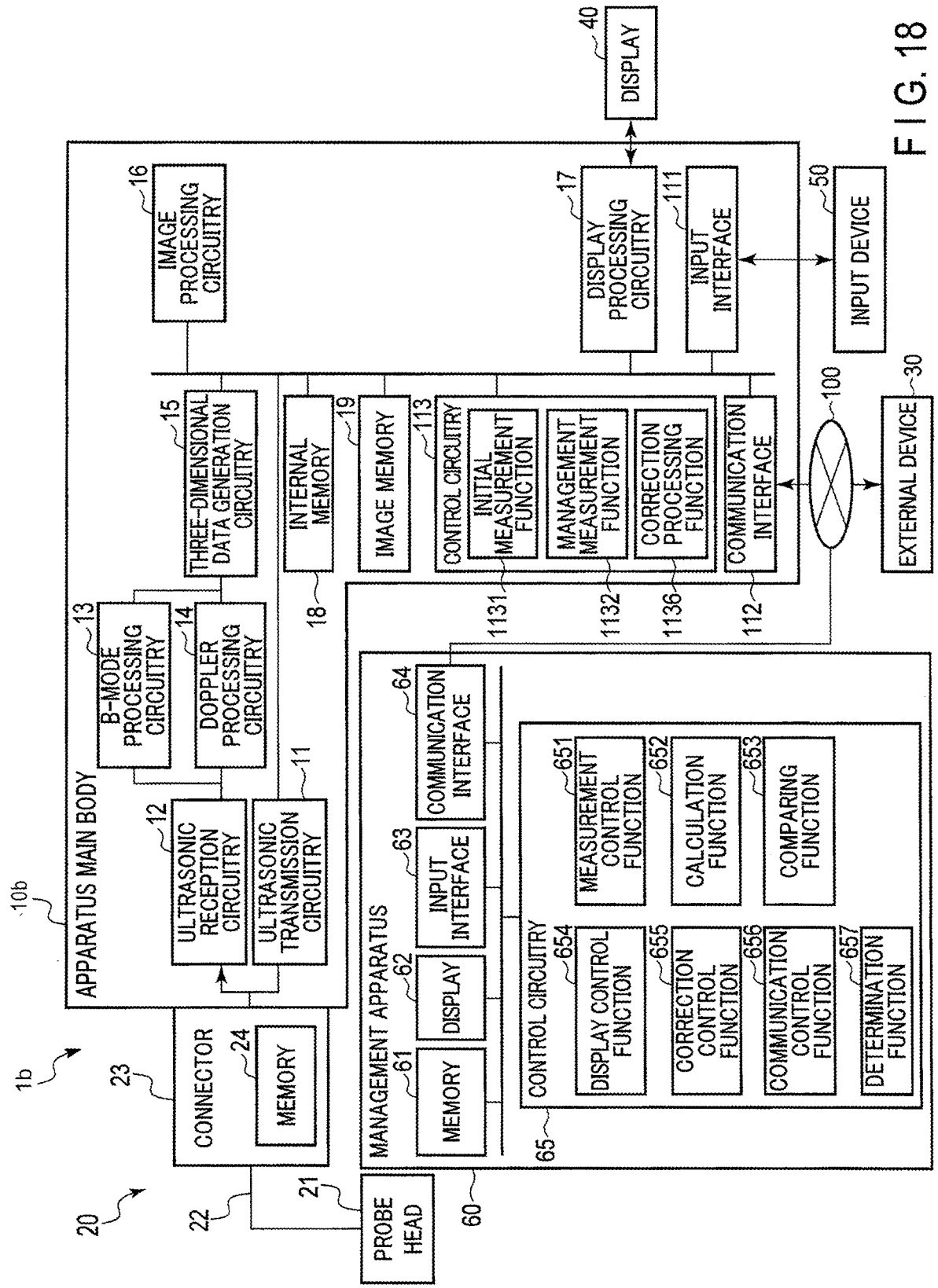
FIG. 18 is a block diagram showing the arrangement of a probe sensitivity management system according to the second embodiment.

FIG. 18 is a block diagram showing an example of the arrangement of a probe sensitivity management system according to the second embodiment. The probe sensitivity management system shown in FIG. 18 includes an ultrasonic diagnostic apparatus 1b and the management apparatus 60.

When executing maintenance and inspection, the serviceman connects the management apparatus 60 to the ultrasonic diagnostic apparatus 1b wirelessly or wiredly, and manages the sensitivity of an ultrasonic probe 20 of the ultrasonic diagnostic apparatus 1. The management apparatus 60 includes memory 61, a display 62, an input interface 63, a communication interface 64, and the control circuitry 65.

The memory 61 includes, for example, a storage medium or the like that is readable by a processor, such as a magnetic or optical storage medium or semiconductor memory. The memory 61 stores a program or the like for managing the sensitivity of the ultrasonic probe 20.

The input interface 63 is a mouse, keyboard, panel switch, operation panel, or the like, which receives various types of instructions from the user. The input interface 63 is connected to the control circuitry 65 via, for example, a bus, converts an operation instruction input from the operator into an electrical signal, and outputs the electrical signal to the control circuitry 65.

The communication interface 64 is connected to an apparatus main body 10b wirelessly or wiredly and performs data communication with an apparatus main body 10b.

The control circuitry 65 is, for example, a processor functioning as the central unit of the management apparatus 60. The control circuitry 65 executes a program for managing the sensitivity of the ultrasonic probe 20, which is stored in the memory 61, to implement a function corresponding to the program. The control circuitry 65 includes, for example, a measurement control function 651, a calculation function 652, a comparing function 653, a display control function 654, and a correction control function 655.

The measurement control function 651 is a function of causing the ultrasonic diagnostic apparatus 1b to measure the sensitivity of the ultrasonic probe 20. More specifically, for example, the control circuitry 65 executes the measurement control function 651 upon receiving an instruction to start managing the sensitivity of the ultrasonic probe 20. Upon executing the measurement control function 651, the control circuitry 65 causes the apparatus main body 10b to measure the sensitivity of the ultrasonic probe 20.

The calculation function 652 is a function of calculating feature values based on reflected wave signals acquired by the ultrasonic diagnostic apparatus 1b. More specifically, for example, the control circuitry 65 executes the calculation function 652 when the ultrasonic diagnostic apparatus 1b outputs a reflected wave signal for each channel. Upon executing the calculation function 652, the control circuitry 65 calculates feature values by analyzing the reflected wave system of the reflected wave signals.

The comparing function 653 is a function of comparing the feature values acquired at two different time points. More specifically, for example, upon executing the comparing function 653, the control circuitry 65 compares feature values read out from the ultrasonic diagnostic apparatus 1b with feature values obtained by measurement.

The display control function 654 is a function of displaying a feature value comparison result on the display 62. More specifically, for example, upon executing the display control function 654, the control circuitry 65 causes the display 62 to display a feature value comparison result.

The correction control function 655 is a function of controlling the correction of variations in sensitivity between ultrasonic transducers 211 of the ultrasonic probe 20. More specifically, for example, upon executing the correction control function 655, the control circuitry 65 outputs an instruction to the ultrasonic diagnostic apparatus 1b to correct variations in sensitivity between the ultrasonic transducers 211 provided for the ultrasonic probe 20 based on a feature value comparison result. A control circuitry 113 of the ultrasonic diagnostic apparatus 1b corrects variations in sensitivity between the ultrasonic transducers 211 provided for the ultrasonic probe 20 based on the instruction output from the management apparatus 60.

FIG. 19 shows an example of a flowchart when the control circuitry 65 shown in FIG. 18 causes the display 62 to display information concerning the sensitivity of the ultrasonic probe 20.

First of all, when performing maintenance and inspection of the ultrasonic diagnostic apparatus 1b, the serviceman of the ultrasonic diagnostic apparatus 1b inputs an instruction to start the processing of managing the sensitivity of the ultrasonic probe 20 via the input interface 63 of the management apparatus 60. Upon receiving the start instruction, the control circuitry 65 of the management apparatus 60 executes the measurement control function 651. Upon executing the measurement control function 651, the control circuitry 65 outputs an instruction to measure the sensitivity of the ultrasonic probe 20 to the apparatus main body 10b (step S191).

Upon receiving a measurement instruction from the management apparatus 60, the control circuitry 113 of the apparatus main body 10b executes a management measurement function 1132. Upon executing the management measurement function 1132, the control circuitry 113 measures the transmission/reception sensitivity of an arbitrary channel of the ultrasonic probe 20 in accordance with measurement condition information stored in the memory 24. The apparatus main body 10b outputs the waveform information of the reflected wave signals obtained by measurement and the initial data stored in the memory 24 to the management apparatus 60.

The control circuitry 65 of the management apparatus 60 receives the waveform information and the initial data output from the apparatus main body 10b (step S192). Upon receiving the waveform information and the initial data, the control circuitry 65 executes the calculation function 652. Upon executing the calculation function 652, the control circuitry 65 calculates the same type of feature value as that of the feature value stored as the initial data based on the waveform information (step S193). The control circuitry 65 outputs the calculated feature values to the ultrasonic diagnostic apparatus 1b and causes the memory 24 of the ultrasonic diagnostic apparatus 1b to store the feature values and measurement condition information at the time of the acquisition of the feature values. In this case, the feature values and the measurement condition information stored in the memory 24 can be used for the measurement of the transmission/reception sensitivity of the ultrasonic probe 20 at a later time point. Note that in evaluation measurement at a later time point, the feature values in the initial data may be set as a reference or the feature values acquired at a predetermined time point after shipment may be set as a reference.

Subsequently, the control circuitry 65 executes the comparing function 653. Upon executing the comparing function 653, the control circuitry 65 compares the feature values included in the initial data with the calculated feature values (step S194). Upon comparing the feature values included in the initial data with the calculated feature values, the control circuitry 65 executes the display control function 654. Upon executing the display control function 654, the control circuitry 65 causes the display 62 to display an image concerning the feature value comparison result (step S195).

Note that the comparison result displayed on the display 62 is not limited to the comparison result between feature values at two time points and may be the comparison result between feature values at a plurality of times points more than three time points. The control circuitry 65 reads out the feature values included in the initial data and the feature values acquired at an arbitrary time point after shipment from the memory 24. The control circuitry 65 compares the readout feature values with the calculated feature values.

The image which the control circuitry 65 causes the display 62 to display is not limited to a comparison result. The control circuitry 65 may read out measurement condition information from the ultrasonic diagnostic apparatus 1b and cause the display 62 to display the readout measurement conditions together with the comparison result. The control circuitry 65 may also cause the display 62 to display the use history of the ultrasonic probe 20 in the time interval from a past time point when sensitivity measurement was executed to the current time point together with a comparison result.

The control circuitry 65 may also output the comparison result as comparison result information to the apparatus main body 10b via the communication interface 64 as well as displaying the comparison result on the display 62. The control circuitry 113 of the apparatus main body 10b stores the comparison result information output from the management apparatus 60 in the internal memory 18.

A flowchart when the control circuitry 65 causes the display 62 to display information concerning the sensitivity of the ultrasonic probe 20 is not limited to that shown in FIG. 19. For example, upon comparing the feature values included in the initial data with the calculated feature values (step S194), the control circuitry 65 determines whether the sensitivity of the ultrasonic probe 20 has deteriorated before the execution of the display control function 654. Upon comparing the feature values included in the initial data with the calculated feature values, the control circuitry 65 executes a determination function 656. Upon executing the determination function 656, the control circuitry 65 determines, based on the feature value comparison result, whether the sensitivity of the ultrasonic probe 20 has deteriorated. Upon determining that the sensitivity of the ultrasonic probe 20 has deteriorated, the control circuitry 65 executes the display control function 654 and displays the comparison result on the display 62. In contrast, upon determining that the sensitivity of the ultrasonic probe 20 has not deteriorated, the control circuitry 65 displays, on the display 62, information indicating that the sensitivity has not deteriorated.

FIG. 20 shows an example of a flowchart when the control circuitry 65 shown in FIG. 18 instructs the ultrasonic diagnostic apparatus 1b to correct the sensitivity of the ultrasonic probe 20.

As indicated by step S194 in FIG. 19, upon comparing the feature values included in the initial data with the calculated feature values, the control circuitry 65 executes the correction control function 655. Upon executing the correction control function 655, the control circuitry 65 outputs an instruction to the ultrasonic diagnostic apparatus 1b to correct variations in sensitivity between the ultrasonic transducers 211 provided for the ultrasonic probe 20 based on the feature value comparison result.

More specifically, the control circuitry 65 calculates a reference value from the feature values included in the initial data read out from the ultrasonic diagnostic apparatus 1b (step S201). The control circuitry 65 outputs, for example, an instruction to correct the sensitivity of the ultrasonic probe 20 to the ultrasonic diagnostic apparatus 1b, together with the feature values obtained by measurement and the calculated reference value (step S202).

Upon receiving the correction instruction from the management apparatus 60, the control circuitry 113 of the apparatus main body 10b executes a correction processing function 1136. Upon executing the correction processing function 1136, the control circuitry 113 corrects variations in sensitivity between the ultrasonic transducers 211 so as to make the feature values to be obtained by measurement almost coincide with the calculated reference value. The control circuitry 113 stores information after the correction in the measurement condition information stored in the memory 24. More specifically, for example, the control circuitry 113 changes the driving voltage of the pulser circuitry of ultrasonic transmission circuitry 11 for each channel based on the reference value, and stores the value obtained by changing the driving voltage of the pulser circuitry in the measurement condition information stored in the memory 24.

A flowchart when the control circuitry 65 instructs the ultrasonic diagnostic apparatus 1b to correct the sensitivity of the ultrasonic probe 20 is not limited to that shown in FIG. 20. For example, upon comparing the feature values included in the initial data with the calculated feature values (step S194), the control circuitry 65 may determine whether the sensitivity of the ultrasonic probe 20 has deteriorated, that is, correction processing needs to be executed, before the execution of the correction control function 655. Upon comparing the feature values included in the initial data with the calculated feature values, the control circuitry 65 executes the determination function 656. Upon executing the determination function 656, the control circuitry 65 determines the necessity of correction processing for the ultrasonic transducer 211 based on the feature value comparison result. The control circuitry 65 executes the correction control function 655 for the ultrasonic transducer 211 requiring correction processing.

The processing for correcting variations in sensitivity between the ultrasonic transducers 211 is not limited to correction based on a reference value. The control circuitry 113 may correct variations in sensitivity between the ultrasonic transducers 211 through re-polarization of the ultrasonic transducers 211.

As described above, in the second embodiment, the control circuitry 113 of the ultrasonic diagnostic apparatus 1b stores information concerning reflected wave signals in the memory 24 of the ultrasonic probe 20 at a first time point as a manufacture/shipment time or a predetermined time point after the manufacture/shipment.

The information concerning the reflected wave signals includes, for example, feature values concerning the transmission/reception sensitivity of the ultrasonic probe 20 and measurement conditions at the time of the acquisition of the feature values. The management apparatus 60 is connected to the ultrasonic diagnostic apparatus 1b at the timing of maintenance/inspection (second time point) after the first time point. When the management apparatus 60 is connected to the ultrasonic diagnostic apparatus 1b, the control circuitry 65 of the management apparatus 60 acquires feature values concerning the transmission/reception sensitivity of the ultrasonic probe 20 based on the measurement conditions stored in the memory 24. The control circuitry 65 then displays, on the display 62, the comparison result between the initial feature values stored in the memory 24 and the newly acquired feature values. This makes it possible for the management apparatus 60 to immediately notify the operator of a change in the transmission/reception sensitivity of the ultrasonic probe 20 after the lapse of a predetermined period since shipment. This allows the operator to quickly cope with the deterioration of the ultrasonic probe 20, thereby improving service performance.

In the second embodiment, the control circuitry 65 determines whether the sensitivity of the ultrasonic probe 20 has deteriorated. If the sensitivity has deteriorated, the control circuitry 65 displays a comparison result on the display 62. If the sensitivity has not deteriorated, the control circuitry 65 displays corresponding information on the display 62. This allows the operator to easily determine whether the transmission/reception sensitivity of the ultrasonic probe 20 has deteriorated.

In the second embodiment, the control circuitry 65 causes the ultrasonic diagnostic apparatus 1b to correct variations in sensitivity between the ultrasonic transducers 211 provided for the ultrasonic probe 20 based on a feature value comparison result. This makes it possible to suppress variations in sensitivity between the ultrasonic transducers 211 while recovering the sensitivity of the ultrasonic probe 20 to a sensitivity almost equal to the sensitivity regarded as a reference.

In the second embodiment, the control circuitry 65 compares the feature values acquired at two time points to determine whether correction processing is necessary for the ultrasonic transducer 211. If the correction processing is necessary, the control circuitry 65 causes the ultrasonic diagnostic apparatus 1b to correct variations in sensitivity between the ultrasonic transducers 211. This makes it possible to correct variations in sensitivity between the ultrasonic transducers 211 with respect to the ultrasonic probe 20 whose transmission/reception sensitivity has deteriorated in the time interval from the first time point to the second time point, thereby suppressing a processing load on the ultrasonic diagnostic apparatus 1b.

Note that in the second embodiment as well, the control circuitry 113 may cause the memory 24 to store waveform information of reflected wave signals received at the manufacture/shipment time or a predetermined time point after the manufacture/shipment. In addition, the memory 24 of the ultrasonic probe 20 may be substituted by the internal memory 18 provided in the apparatus main body 10b or a memory provided in the external device 30.

The ultrasonic diagnostic apparatuses 1 and 1a and the probe sensitivity management system according to the above embodiments can correct the temporal deterioration of an ultrasonic probe. In addition, the ultrasonic diagnostic apparatuses 1 and 1a and the probe sensitivity management system can evaluate the temporal deterioration of an ultrasonic probe.

The term "processor" used in the above description of each embodiment means, for example, a CPU (Central Processing Unit), a GPU (Graphics Processing Unit), or circuitry such as an ASIC (Application Specific Integrated Circuit), or a programmable logic device (for example, SPLD (Simple Programmable Logic Device), CPLD (Complex Programmable Logic Device), or FPGA (Field Programmable Logic Device)). The processor implements a function by reading out and executing a program saved in the storage circuitry. Note that a program may be directly incorporated in the circuitry of a processor instead of being stored in storage circuitry. In this case, the processor implements a function by reading out and executing a program incorporated in the circuitry of the processor. Note that each processor according to each embodiment described above may be formed as a single processor to implement its function by combining a plurality of independent circuits in addition of being formed as single circuitry for each processor. In addition, a plurality of constituent elements in each embodiment described above may be integrated into a single processor to implement its function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
an ultrasonic probe including a plurality of ultrasonic transducers;
a memory; and
processing circuitry configured to:
measure initial data relating to sensitivity of the ultrasonic probe including first reflected wave signals generated by the ultrasonic probe at a first time point during a period from a manufacture of the apparatus to shipment;
store information concerning the first reflected wave signals in the memory;
measure second reflected wave signals generated by the ultrasonic probe at a second time point after the first time point, the second time point being for inspection of deterioration of the sensitivity;
perform correction to suppress variations between the second reflected wave signals respectively generated by the plurality of ultrasonic transducers based on the information concerning the first reflected wave signals stored in the memory and information concerning the second reflected wave signals acquired based on the measurement of the second reflected wave signals;
display use history of the ultrasonic probe in a time interval from the first time point to the second time point; and notify a user of a forecast timing at which the information concerning the second reflected wave signals does not reach a manufacture reference value if a deterioration tendency of the sensitivity of the ultrasonic probe is maintained.

2. The ultrasonic diagnostic apparatus according to claim 1, wherein the processing circuitry determines a necessity of correction processing based on the information concerning the first reflected wave signals and the information concerning the second reflected wave signals, and performs correction to suppress the variations in accordance with a determination result indicating that the correction processing is necessary.

3. The ultrasonic diagnostic apparatus according to claim 2, wherein the processing circuitry performs correction to suppress the variations based on a reference value calculated from the information concerning the first reflected wave signals or the information concerning the second reflected wave signals.

4. The ultrasonic diagnostic apparatus according to claim 2, wherein the processing circuitry performs correction to suppress the variations based on a reference value calculated from the information concerning the first reflected wave signals or the information concerning the second reflected wave signals after re-polarization of at least one of the plurality of ultrasonic transducers by reactivation of at least one of the plurality of ultrasonic transducers.

5. The ultrasonic diagnostic apparatus according to claim 1, wherein the processing circuitry performs correction to suppress the variations based on a reference value calculated from the information concerning the first reflected wave signals.

6. The ultrasonic diagnostic apparatus according to claim 1, wherein the processing circuitry performs correction to suppress the variations based on a reference value calculated from the information concerning the first reflected wave signals after re polarization of at least one of the plurality of ultrasonic transducers.

7. The ultrasonic diagnostic apparatus according to claim 1, wherein the processing circuitry calculates first feature values at the first time point based on the measured first reflected wave signals, stores the first feature values as the information concerning the first reflected wave signals in the memory, calculates second feature values at the second time point based on the measured second reflected wave signals to set the second feature values as the information concerning the second reflected signals.

8. The ultrasonic diagnostic apparatus according to claim 1, wherein the processing circuitry stores waveform information of the measured first reflected wave signals as the information concerning the first reflected wave signals in the memory at the first time point, calculates first feature values based on the waveform information stored in the memory at the second time point to include the first feature values in the information concerning the first reflected wave signals, and calculates second feature values based on the measured second reflected wave signals at the second time point to set the second feature values as the information concerning the second reflected wave signals.

9. The ultrasonic diagnostic apparatus according to claim 1, wherein the processing circuitry compares the information concerning the first reflected wave signals stored in the memory with the information concerning the second reflected wave signals, and notifies, via a display, a user of a comparison result between the information concerning the first reflected wave signals and the information concerning the second reflected wave signals.

10. The ultrasonic diagnostic apparatus according to claim 9, wherein the processing circuitry further stores the information concerning the second reflected wave signals in the memory, measures third reflected wave signals generated by the ultrasonic probe at a third time point after the second time point, compares at least one of the information concerning the first reflected wave signals and the information concerning the second reflected wave signals stored in the memory with the information concerning the third reflected wave signals, and notifies a user of a comparison result between at least one of the information concerning the first reflected wave signals and the information concerning the second reflected wave signals with the information concerning the third reflected wave signals.

11. The ultrasonic diagnostic apparatus according to claim 1, wherein the memory stores a preset manufacture reference value, and the processing circuitry compares the manufacture reference value stored in the memory with the information concerning the second reflected wave signals, and notifies a user of a comparison result between the manufacture reference value and the information concerning the second reflected wave signals.

12. The ultrasonic diagnostic apparatus according to claim 11, wherein the processing circuitry notifies the user of a timing at which the information concerning the second reflected wave signals do not reach the manufacture reference value.

13. The ultrasonic diagnostic apparatus according to claim 9, wherein the processing circuitry determines whether the ultrasonic probe has deteriorated, based on the information concerning the first reflected wave signals and the information concerning the second reflected wave signals, and notifies the comparison result in accordance with a determination result indicating that the ultrasonic probe has deteriorated.

14. A probe sensitivity management system comprising:
an ultrasonic probe;
a memory; and
processing circuitry configured to:
  measure initial data relating to sensitivity of the ultrasonic probe including first reflected wave signals generated by the ultrasonic probe at a first time point during a period from a manufacture of the system to shipment;
  store information concerning the first reflected wave signals in the memory;
  measure second reflected wave signals generated by the ultrasonic probe at a second time point after the first time point, the second time point being for inspection of deterioration of the sensitivity;
  perform correction to suppress variations between the second reflected wave signals respectively generated by the ultrasonic probe based on the information concerning the first reflected wave signals stored in the memory and information concerning the second reflected wave signals acquired based on the measurement of the second reflected wave signals;
  display use history of the ultrasonic probe in a time interval from the first time point to the second time point; and
  notify a user of a forecast timing at which the information concerning the second reflected wave signals does not reach a manufacture reference value if a deterioration tendency of the sensitivity of the ultrasonic probe is maintained.

15. A non-transitory storage medium storing a program that causes processing circuitry to execute a process of measuring initial data relating to sensitivity of an ultrasonic probe including first reflected wave signals generated by an ultrasonic probe at a first time point during a period from a manufacture of an apparatus comprising the processing circuitry to shipment, a process of storing information concerning the first reflected wave signals in a memory, a process of measuring second reflected wave signals generated by the ultrasonic probe at a second time point after the first time point, the second time point being for inspection of deterioration of the sensitivity, a process of performing correction to suppress variations between second reflected wave signals respectively generated by the ultrasonic probe based on the information concerning the first reflected wave signals stored in the memory and information concerning the second reflected wave signals acquired based on the measurement of the second reflected wave signals;

a process of displaying use history of the ultrasonic probe in a time interval from the first time point to the second time point; and a process of notifying a user of a forecast timing at which the information concerning the second reflected wave signals does not reach a manufacture reference value if a deterioration tendency of the sensitivity of the ultrasonic probe is maintained.

16. The ultrasonic diagnostic apparatus according to claim 11, wherein the processing circuitry selects a channel whose transmission/reception sensitivity is to be measured based on a contribution to image quality.

* * * * *